US010842472B2

(12) United States Patent
Kapushion

(10) Patent No.: US 10,842,472 B2
(45) Date of Patent: Nov. 24, 2020

(54) BIOPSY DEVICE WITH AUTOMATIC BIOPSY PARAMETER ADJUSTMENT

(71) Applicant: HOLOGIC, INC., Marlborough, MA (US)

(72) Inventor: Joseph Kapushion, Erie, CO (US)

(73) Assignee: Hologic, Inc., Marlborough, MA (US)

(*) Notice: Subject to any disclaimer, the term of this patent is extended or adjusted under 35 U.S.C. 154(b) by 330 days.

(21) Appl. No.: 16/027,155

(22) Filed: Jul. 3, 2018

(65) Prior Publication Data
US 2018/0317894 A1 Nov. 8, 2018

Related U.S. Application Data

(63) Continuation of application No. 15/278,667, filed on Sep. 28, 2016, now Pat. No. 10,016,184, which is a continuation of application No. 14/497,046, filed on Sep. 25, 2014, now Pat. No. 9,456,808.

(51) Int. Cl.
*A61B 5/00* (2006.01)
*A61B 10/02* (2006.01)

(52) U.S. Cl.
CPC ........ *A61B 10/0275* (2013.01); *A61B 5/4312* (2013.01); *A61B 2010/0208* (2013.01); *A61B 2560/0443* (2013.01); *A61B 2562/0223* (2013.01)

(58) Field of Classification Search
CPC ............... A61B 10/02; A61B 10/0275; A61B 2010/0208; A61B 5/4312; A61B 2560/0443; A61B 2562/0223
See application file for complete search history.

(56) References Cited

U.S. PATENT DOCUMENTS

| | | |
|---|---|---|
| 4,702,261 A | 10/1987 | Cornell et al. |
| 5,036,860 A | 8/1991 | Leigh et al. |
| 5,120,463 A | 6/1992 | Bjork et al. |
| 5,165,136 A | 11/1992 | Moore |
| 5,313,958 A | 5/1994 | Bauer |
| 5,916,175 A | 6/1999 | Bauer |
| 6,749,576 B2 | 6/2004 | Baur |
| 7,229,419 B2 | 6/2007 | Hancock |
| 7,481,775 B2 | 1/2009 | Weikel et al. |
| 7,517,322 B2 | 4/2009 | Weikel, Jr. et al. |
| 7,717,861 B2 | 5/2010 | Weikel et al. |

(Continued)

*Primary Examiner* — Max F Hindenburg
(74) *Attorney, Agent, or Firm* — Vista IP Law Group, LLP

(57) ABSTRACT

A biopsy system includes an elongate cannula coupled to and extending from a support structure, the cannula having a distal portion with a tissue receiving aperture in a side wall thereof, and an elongate hollow introducer sized and configured to be mounted to the support structure over the cannula. The support structure and a proximal portion of the introducer are respectively configured for providing releasable attachment of the introducer to the support structure over the cannula in a first attachment configuration, in which the distal portion of the cannula extends out an open distal end of the introducer with the tissue receiving aperture unobscured by the introducer, and in a second attachment configuration, in which the distal portion of the cannula extends out the open distal end of the introducer with the tissue receiving aperture partially obscured by the introducer.

16 Claims, 33 Drawing Sheets

(56) References Cited

U.S. PATENT DOCUMENTS

| | | |
|---|---|---|
| 8,088,081 B2 | 1/2012 | Field et al. |
| 8,197,419 B2 | 6/2012 | Field et al. |
| 8,287,466 B2 | 10/2012 | Weikel, Jr. |
| 8,343,070 B2 | 1/2013 | Krueger |
| 9,332,973 B2 | 5/2016 | McWeeney |
| 9,456,808 B2 | 10/2016 | Kapushion |
| 10,016,184 B2 * | 7/2018 | Kapushion ......... A61B 10/0275 |
| 2006/0258953 A1 | 11/2006 | Lee |

* cited by examiner

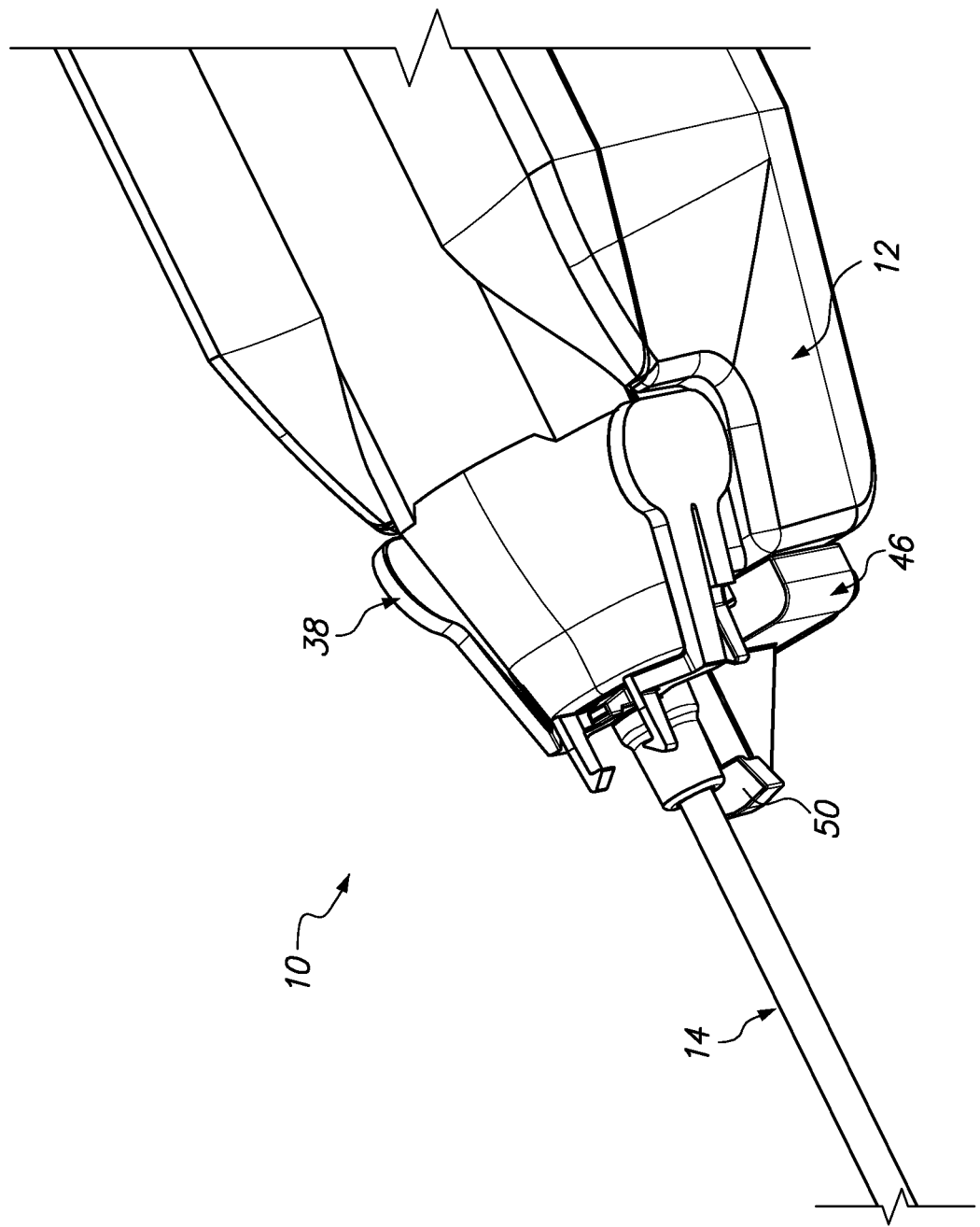

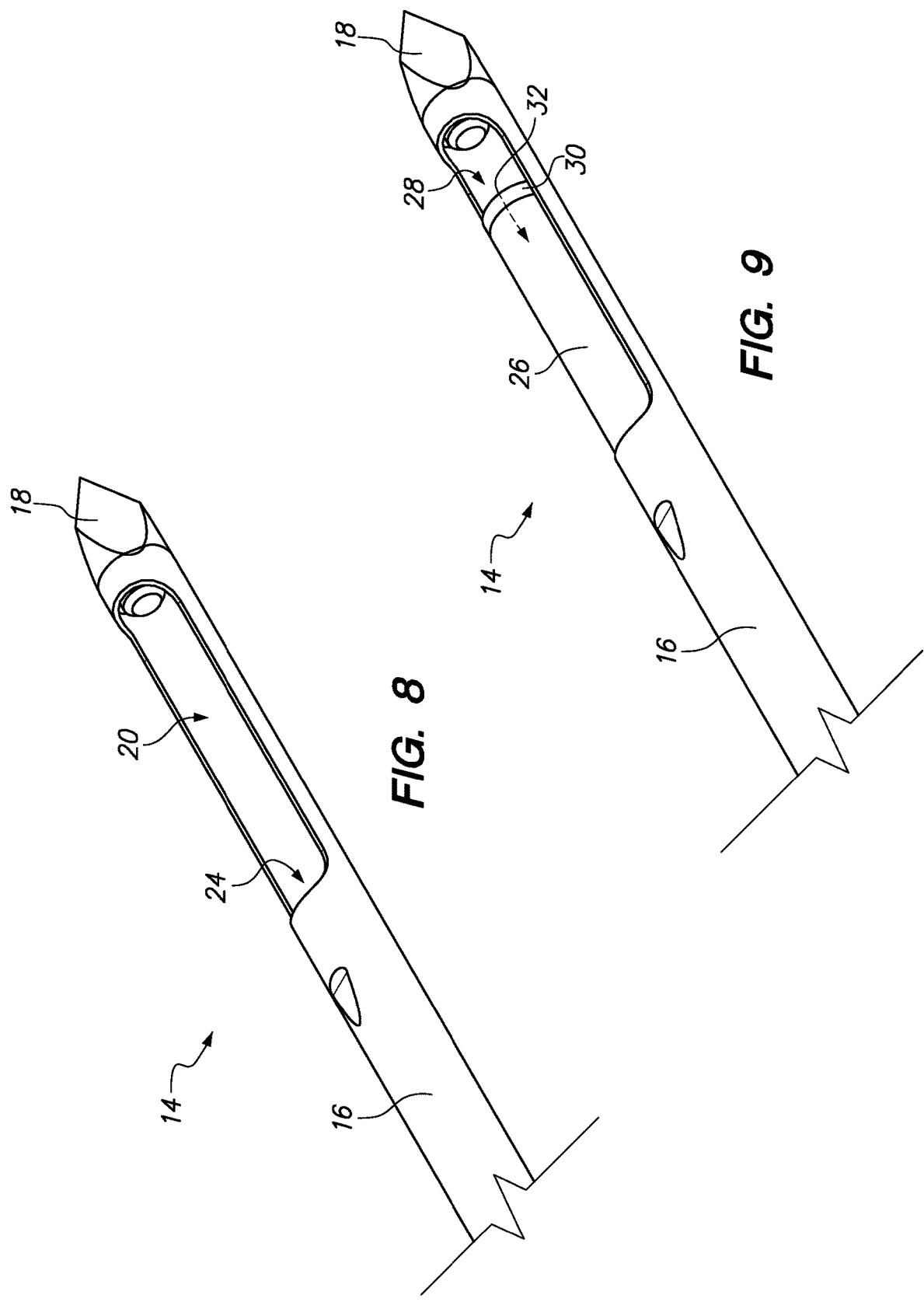

BIOPSY DEVICE WITH AUTOMATIC BIOPSY PARAMETER ADJUSTMENT

RELATED APPLICATION DATA

The present application is a continuation of U.S. patent application Ser. No. 15/278,667, filed Sep. 28, 2016, now U.S. Pat. No. 10,016,184, which is a continuation of U.S. patent application Ser. No. 14/497,046, filed Sep. 25, 2014, now U.S. Pat. No. 9,456,808, the priority of which is claimed under 35 U.S.C. § 120, and the contents of which is incorporated herein by reference in its entirety, as though set forth in full.

FIELD

The present disclosure generally relates to the field of tissue sampling and harvesting. More specifically, the disclosure relates to biopsy needle sets and devices for use therewith.

BACKGROUND

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsies are routinely performed on tissue using a needle set. One known needle set includes an elongate outer cannula having a pointed tip and a tissue receiving aperture defined near its distal end, and an inner cannula having an open distal end surrounded by an annular cutting blade. The inner cannula is slidably disposed within the outer cannula so that it can close the tissue receiving aperture, thereby cutting tissue prolapsing into the lumen of the outer cannula through the tissue receiving aperture. Typically, a tubular introducer is disposed around the outer cannula of a needle set. The typical introducer is a tube with an open end through which the outer cannula extends.

Most biopsies are performed with a standard aperture and a standard stroke length (i.e., the travel distance of the inner cannula inside of the outer cannula). For instance, a 20 mm aperture and a corresponding 23 mm stroke length are typical for vacuum assisted breast biopsy procedures. In some instances, the physician may prefer a smaller aperture and/or a shorter stroke length. One such instance is when a compressed breast measures 20 mm or less. In that case, a 20 mm aperture may not fit inside of the compressed breast, and the tissue piercing tip may exit the far side of the breast or impact the underlying rib cage. The physician may prefer to use a 12 mm aperture to ensure that the aperture and the distal tip, which measures 8 mm, will both fit inside of the compressed breast. A smaller aperture is especially important when the biopsy device must be positioned using stereotactic X-ray guidance.

For a reduced size aperture, a corresponding reduced stroke length of 15 mm increases the efficiency of the biopsy device by reducing the stroke time and biopsy time. Further, reducing the stroke length also reduces the distance between the open distal end 28 of the inner cannula 26 and the tissue receiving aperture 20. This reduced distance, in turn, reduces the amount of liquid, introduced through the annular lumen, which exits through the inner cannula lumen 32, instead of the tissue receiving aperture 20. The irrigation system that introduces liquid (e.g., saline) through the annular lumen between the outer and inner cannulas 16, 26 is described in U.S. Provisional Patent Application Ser. No. 62/055,338, filed on Sep. 25, 2014, and assigned to the same assignee as the instant application, the contents of which are incorporated by reference as though fully set forth herein. Moreover, reducing the stroke length also maximizes the overlap between the inner cannula 26 and the introducer 34, thereby maximizing the structural integrity of the portion of the biopsy device 10 in the tissue.

Current breast biopsy procedures include selecting and setting up a tissue biopsy device with an appropriate aperture and stroke length after the breast is compressed and the size of the compressed breast is determined. This delay in the procedure increases the amount of time a patient's breast must be compressed, thereby increasing the discomfort during the procedure. In other cases, a physician may also decide to use a biopsy device with a smaller aperture and stroke length for various other reasons (e.g., to avoid certain areas).

Current needle sets have adjustable apertures, such as those described in U.S. Pat. No. 6,749,576, the contents of which are incorporated by reference as though fully set forth herein. However, the stroke length is not change, but only "adjusted" by changing the size of the aperture. The distance of travel of the inner cutting cannula remains the same regardless of the size of the aperture. With a smaller aperture, the cutting stroke can be decreased proportionally while still completely severing tissue prolapsing into the smaller aperture.

In some biopsy devices, such as those described in U.S. Pat. No. 7,517,322, the contents of which are incorporated by reference as though fully set forth herein, the stroke length can be manually adjusted to match the adjusted aperture. However, this manual adjustment adds another step to and complicates the tissue biopsy procedure.

SUMMARY

In one embodiment of the disclosed inventions, a biopsy system includes a support structure and an elongate cannula coupled to and extending from the support structure, the cannula having a distal portion with a tissue receiving aperture in a side wall thereof. The biopsy system also includes an elongate hollow introducer sized and configured to be mounted to the support structure over the cannula. The support structure and a proximal portion of the introducer are respectively configured for providing releasable attachment of the introducer to the support structure over the cannula in a first attachment configuration, in which the distal portion of the cannula extends out an open distal end of the introducer with the tissue receiving aperture unobscured by the introducer, and in a second attachment configuration, in which the distal portion of the cannula extends out the open distal end of the introducer with the tissue receiving aperture partially obscured by the introducer.

In some embodiments, the introducer may be switched from the first attachment configuration to the second attachment configuration without removing the introducer from the cannula.

In some embodiments, the biopsy system also includes one or more sensors that detect whether the introducer is attached to the support structure in the first attachment configuration, the second attachment configuration, or neither. The one or more sensors may be configured to detect a locating element coupled to the proximal portion of the introducer, wherein the locating element is in a first position relative to the one or more sensors when the introducer is attached to the support structure in the first attachment configuration, and in a second position relative to the one or more sensors when the introducer is attached to the support structure in the second attachment configuration. The one or more sensors may include laterally spaced apart first and second sensors coupled to or adjacent the support structure. The one or more sensors may include magnetic sensors.

In some embodiments, the biopsy system also includes an axially oscillating cutter disposed in an axial lumen of the cannula. An oscillation stroke length of the cutter when the introducer is attached to the support structure in the first attachment configuration is greater than an oscillation stroke length of the cutter when the introducer is attached to the support structure in the second attachment configuration.

In some embodiments, the cannula is movably coupled to the support structure between a proximal armed position and a distal fired position. A firing distance of the cannula from the armed position to the fired position when the introducer is attached to the support structure in the first attachment configuration is greater than a firing distance of the cannula from the armed position to the fired position when the introducer is attached to the support structure in the second attachment configuration.

In some embodiments, the proximal portion of the introducer includes a first pair of laterally spaced apart connector arms and a second pair of laterally spaced apart connector arms. In the first attachment configuration, the first pair of connector arms mate with a corresponding first pair of laterally spaced apart detent latches on the support structure, and in the second attachment configuration, the second pair of connector arms mate with a corresponding second pair of detent latches on the support structure. The connector arms of the first pair may be axially offset from the connector arms of the second pair, and the first pair of detent latches may be correspondingly axially offset from the second pair of detent latches.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 1 to 7 are various wide and detailed perspective views of a biopsy system, including a biopsy device, an adapter and an introducer, according to one embodiment, with the distal tubular portion of the introducer omitted for clarity. The introducer is coupled to the biopsy device in the standard configuration in FIGS. 1-7.

FIGS. 8 and 10 are perspective views of the outer cannula of the biopsy device depicted in FIGS. 1 to 7. In FIG. 8, the cutting board is omitted for clarity.

FIG. 9 is a perspective view of the inner and outer cannulas of the biopsy device depicted in FIGS. 1 to 7. The cutting board is omitted for clarity.

DETAILED DESCRIPTION OF THE ILLUSTRATED EMBODIMENTS

Figure 1:
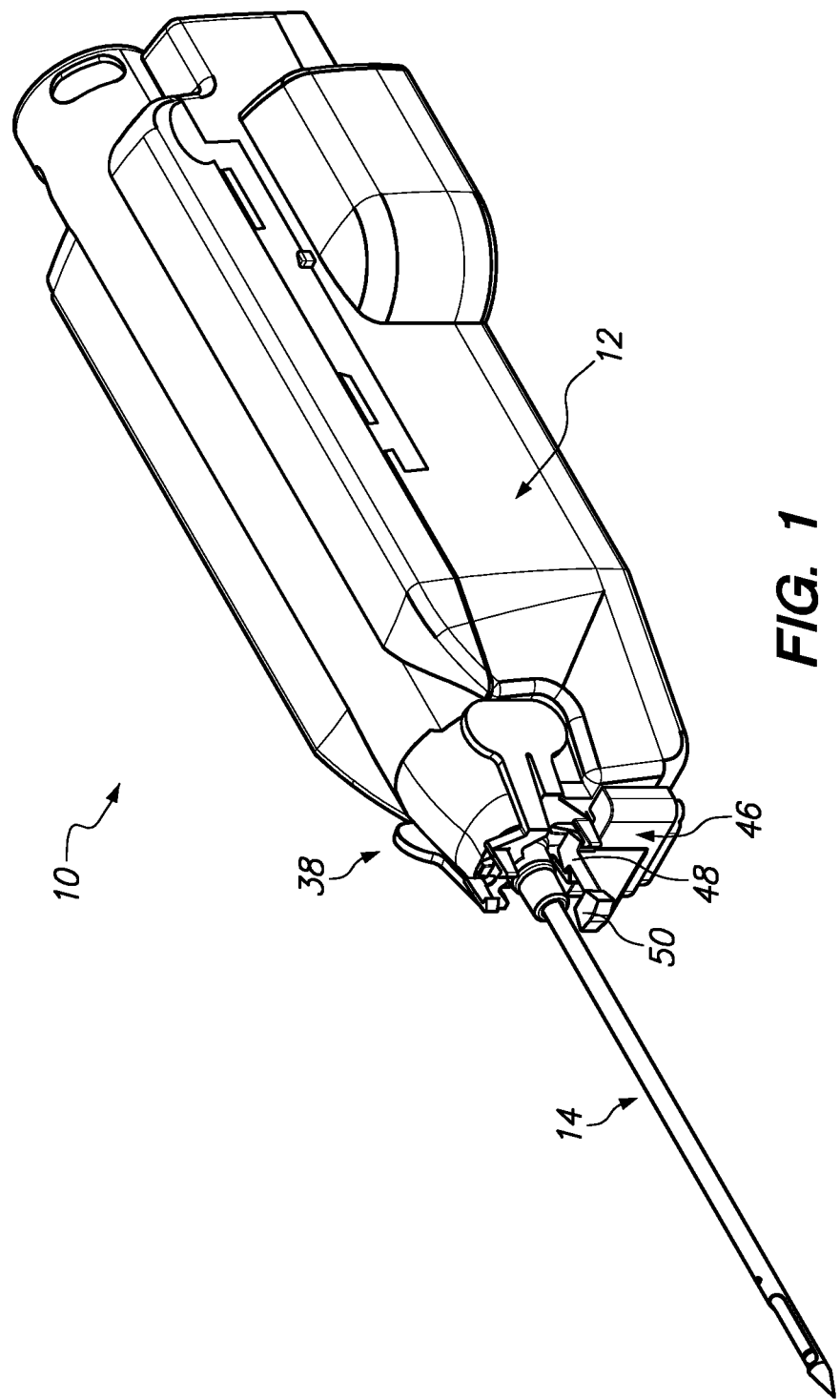
Figure 2:
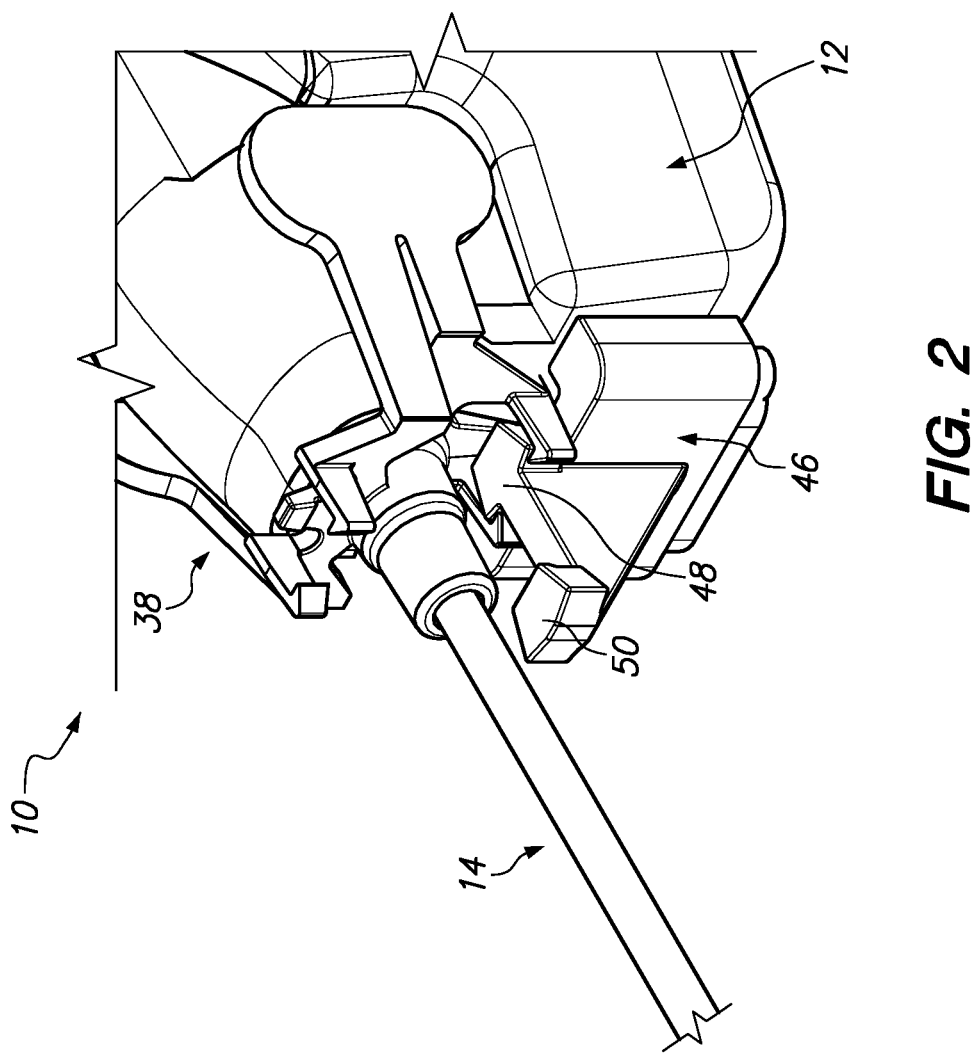
Figure 3:
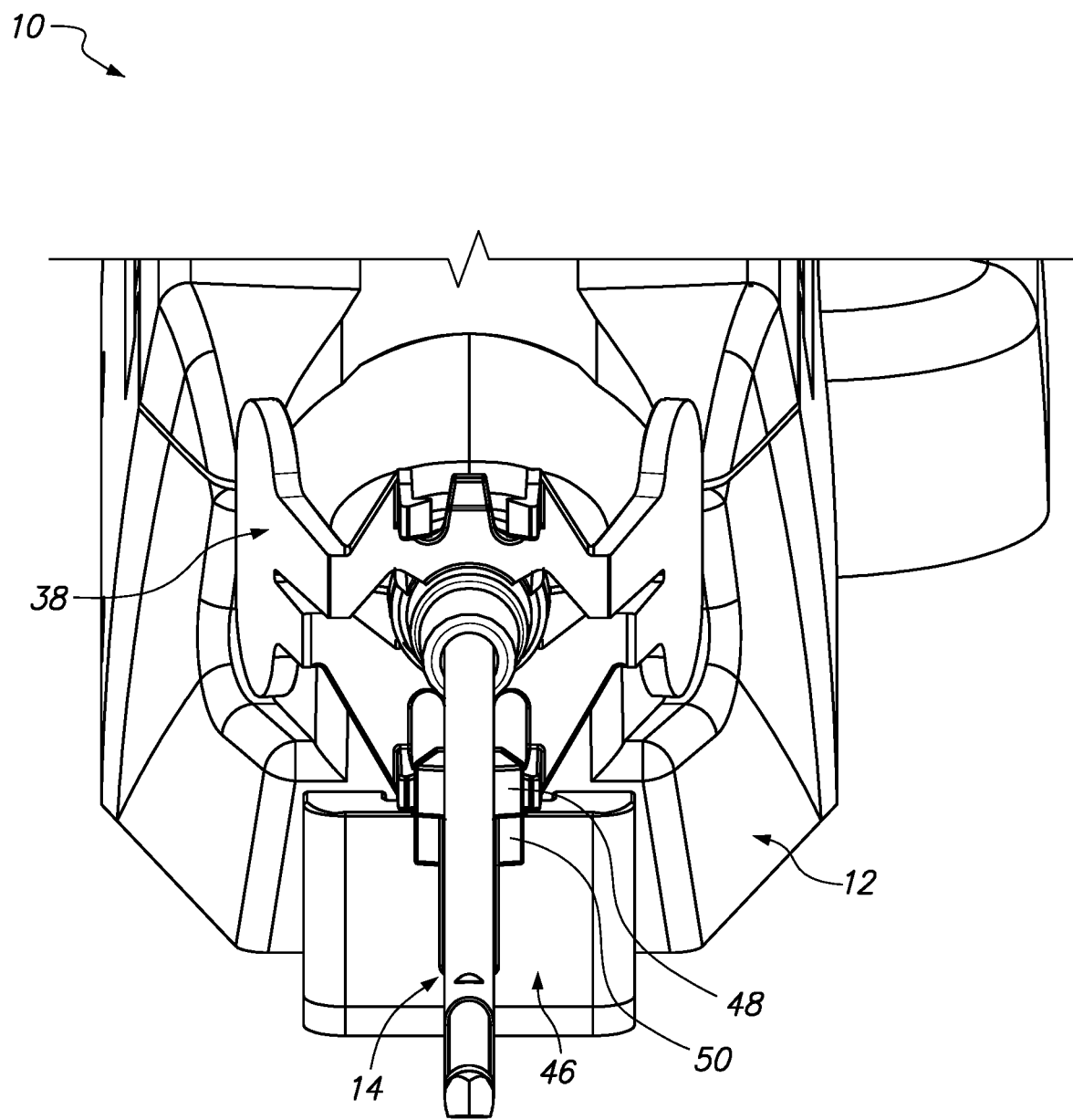
Figure 4:
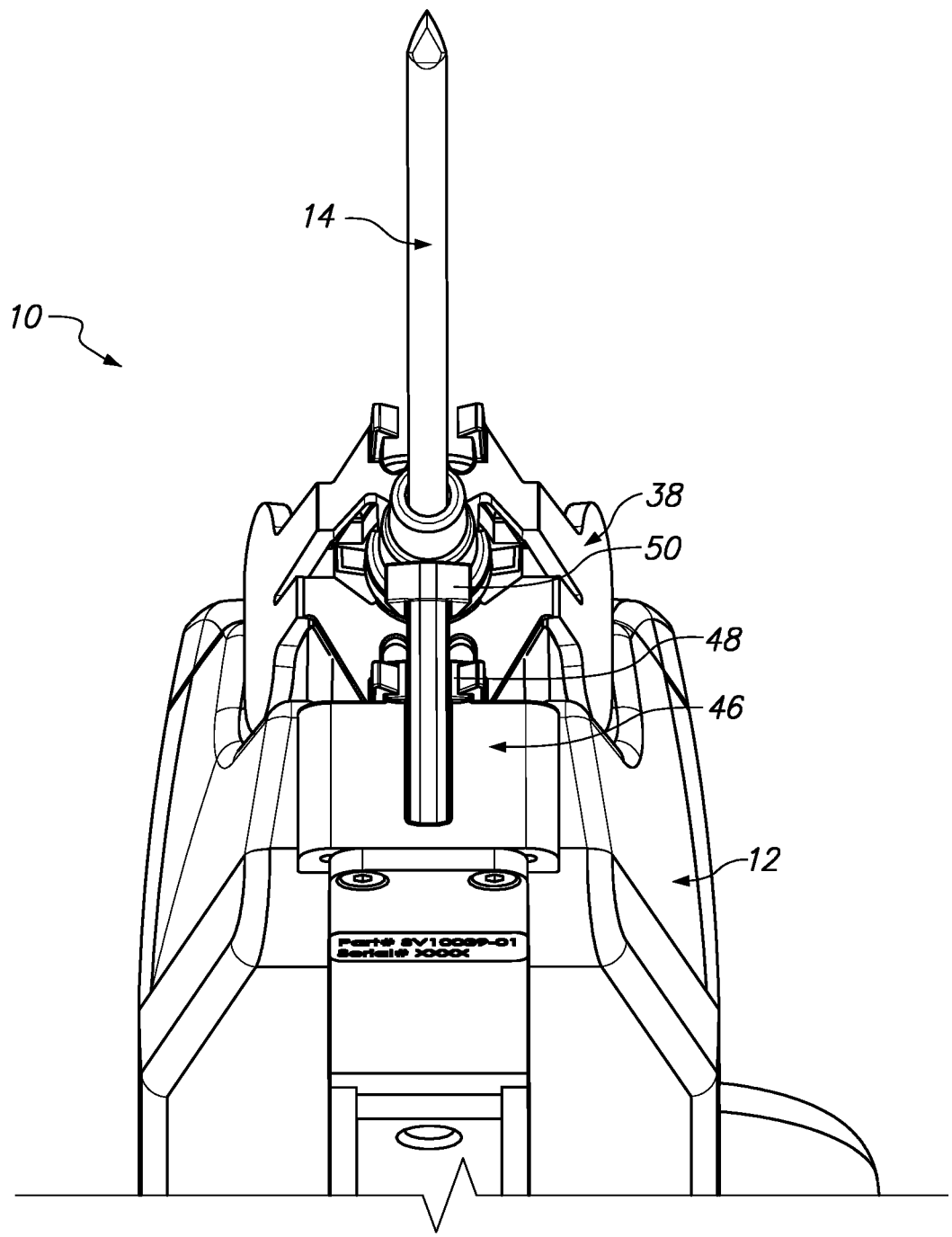
Figure 5:
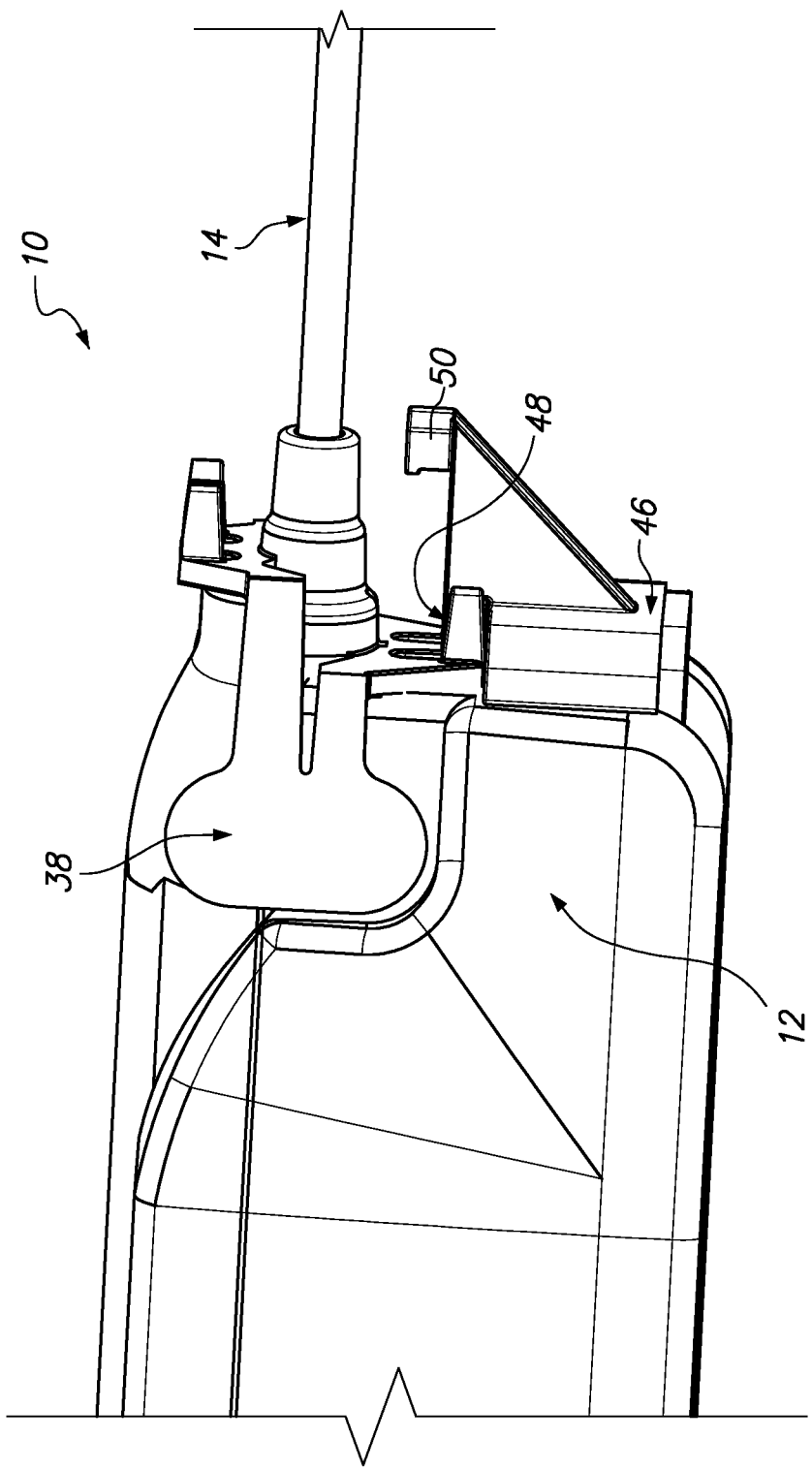
Figure 6:
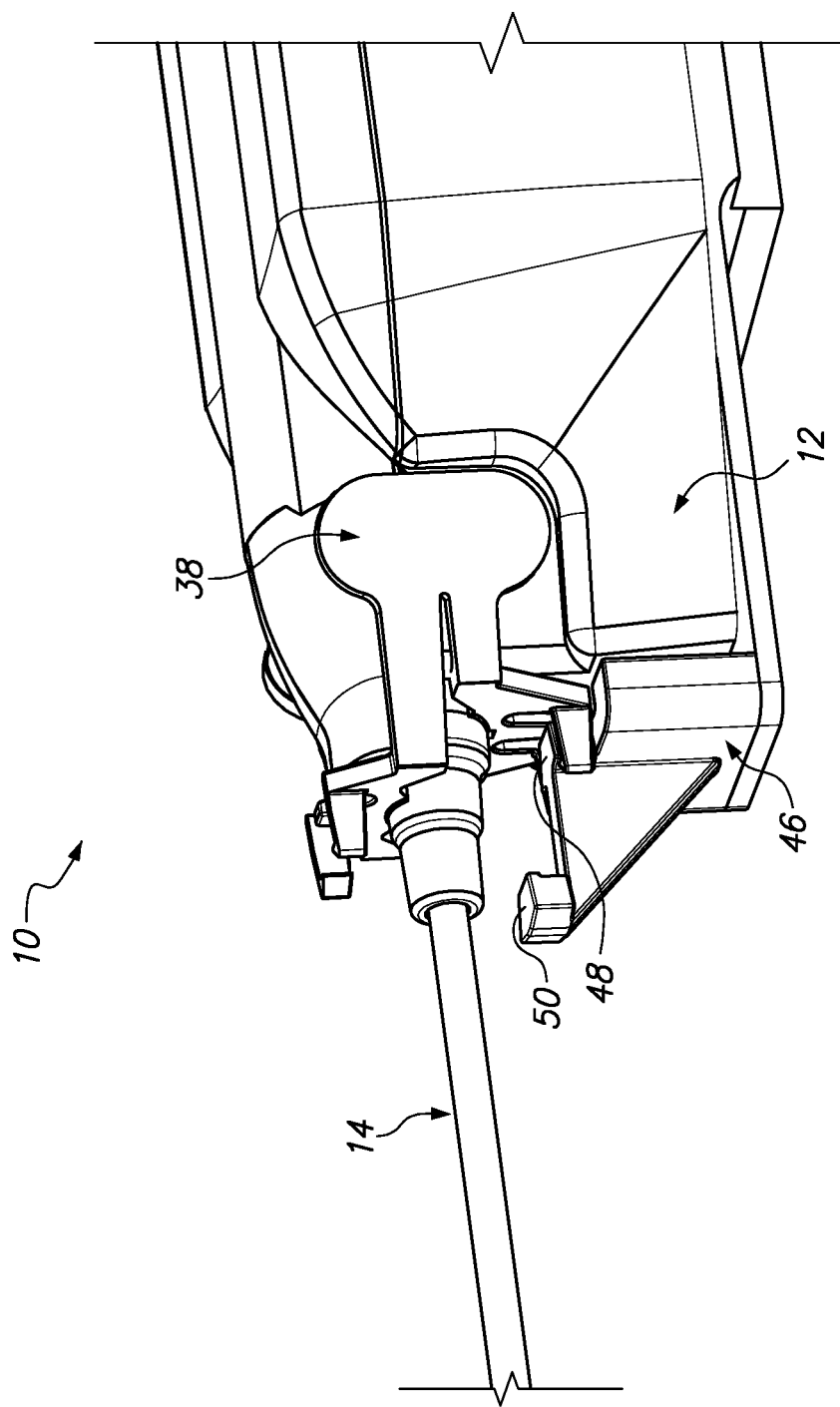

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 1 to 7 depict a biopsy system including a biopsy device 10 in accordance with one embodiment. The biopsy device 10 includes a reusable body portion 12 and a disposable needle portion 14. The body portion 12 includes components configured to perform a tissue biopsy using the needle portion 14. These components include a drive assembly configured to drive movement of components of the needle portion 14. An exemplary drive system is described in U.S. Provisional Patent Application Ser. No. 62/055,610, filed on Sep. 25, 2014, and assigned to the same assignee as the instant application, the contents of which are incorporated by reference as though fully set forth herein. The drive assembly can include one or more motors known in the art, including electrical, pneumatic or hydraulic motors. The body portion 12 also includes a controller (e.g., a computer processor) configured to control the motors in the drive assembly and thereby control movement of the components of the needle portion 14.

FIGS. 8 and 9 depict respective distal portions of the needle portion 14. FIG. 8 shows the outer cannula 16 without the inner cannula 26. FIG. 9 shows the outer cannula 16 with a distal portion of the inner cannula 26 visible through the tissue receiving aperture 20. The needle portion 14 includes an outer cannula 16 having a distal tissue piercing tip 18. The outer cannula defines an outer cannula lumen 24, and a tissue receiving aperture 20 adjacent to the distal tissue piercing tip 18 and in communication with the outer cannula lumen 24. The needle portion 14 also includes an inner cannula 26 slidably disposed in the outer cannula lumen 24, and having an open distal end 28 surrounded by an annular cutting blade 30. When the inner cannula 26 is in its distal-most position in the outer cannula lumen 24, the inner cannula 26 closes the tissue receiving aperture 20 in the outer cannula 16.

Figure 10:
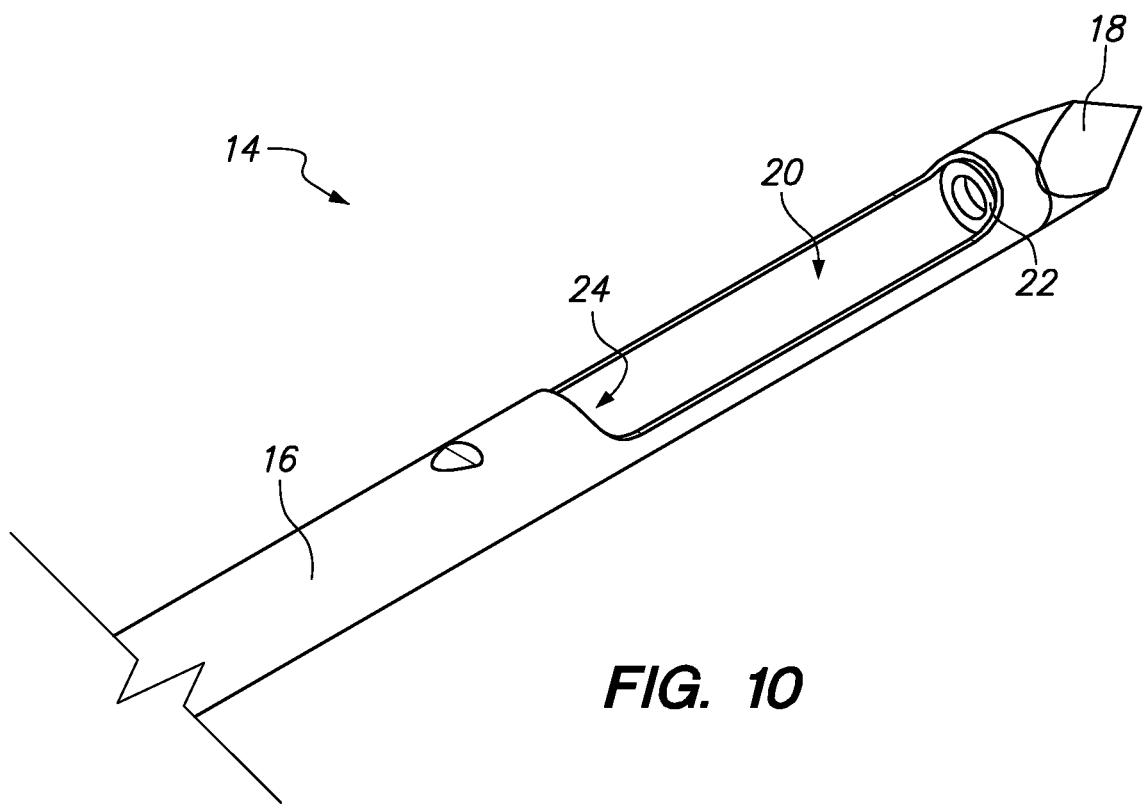
Figure 11:
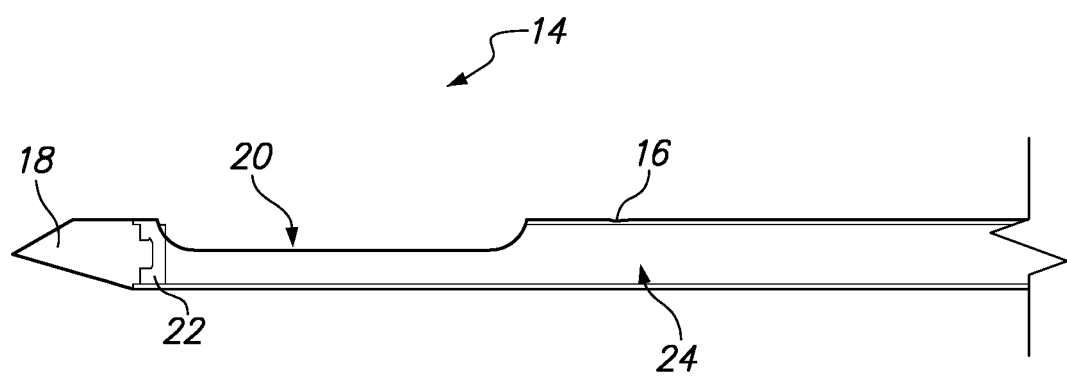
FIG. 11 is a cross-sectional view of the outer cannula of the biopsy device depicted in FIGS. 1 to 7.

As shown in FIGS. 10 and 11, a cutting board 22 is disposed in the outer cannula lumen 24 distal to the tissue receiving aperture 20. The cutting board 22 is configured to seal the open distal end 28 of the inner cannula 26 when the inner cannula 26 is in contact with the cutting board 22. This seal prevents fluids introduced into the outer cannula lumen 24 from being aspirated through the open distal end 28 and the inner cannula lumen 32, and bypassing the biopsy site. Instead, the fluids are delivered to the biopsy site through the outer cannula lumen 24 and the tissue receiving aperture 20.

As shown in FIGS. 12 to 17, the biopsy device 10 is configured to be coupled to an introducer 34 (also included in the biopsy system) defining an introducer lumen 36 in which the needle portion 14 is disposed during certain portions of the tissue biopsy procedure. The introducer 34 includes an introducer hub 38 at a proximal end thereof and an open distal end 40 through which a distal end (including the tissue piercing tip 18 and at least a portion of the tissue receiving aperture 20) of the outer cannula 16 extends during the tissue biopsy procedure. While the introducer hub 38 is depicted in FIGS. 1-7, the distal tubular portion 42 of the introducer 34 is omitted in those figures for clarity.

Figure 12:
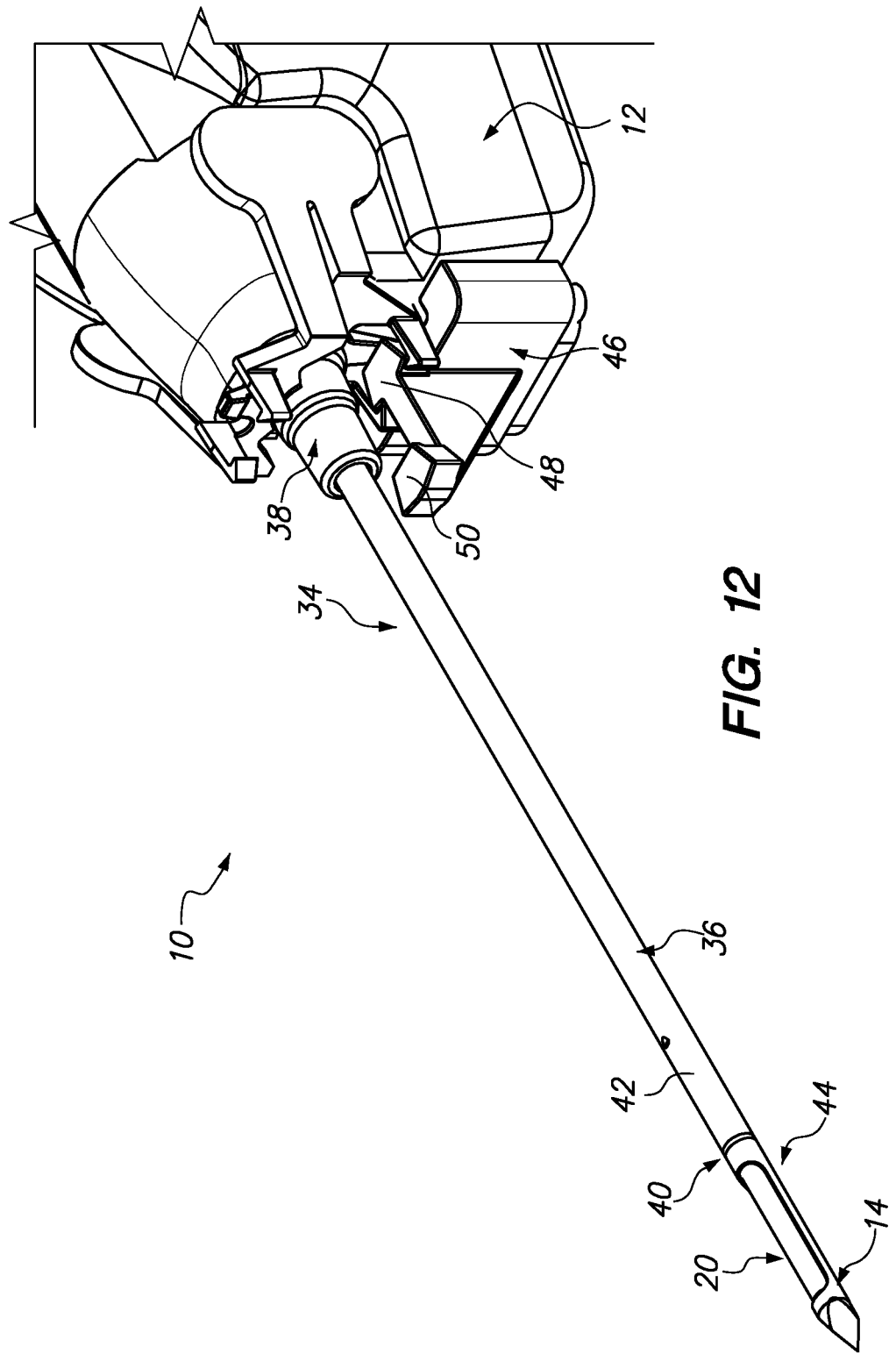
FIGS. 12, 13, 16 and 17 are various detailed perspective views of a biopsy system, including a biopsy device, an adapter and an introducer, according to one embodiment. The introducer is coupled to the biopsy device in the standard configuration in FIGS. 12 and 16. The introducer is coupled to the biopsy device in the petite configuration in FIGS. 13 and 17.
Figure 13:
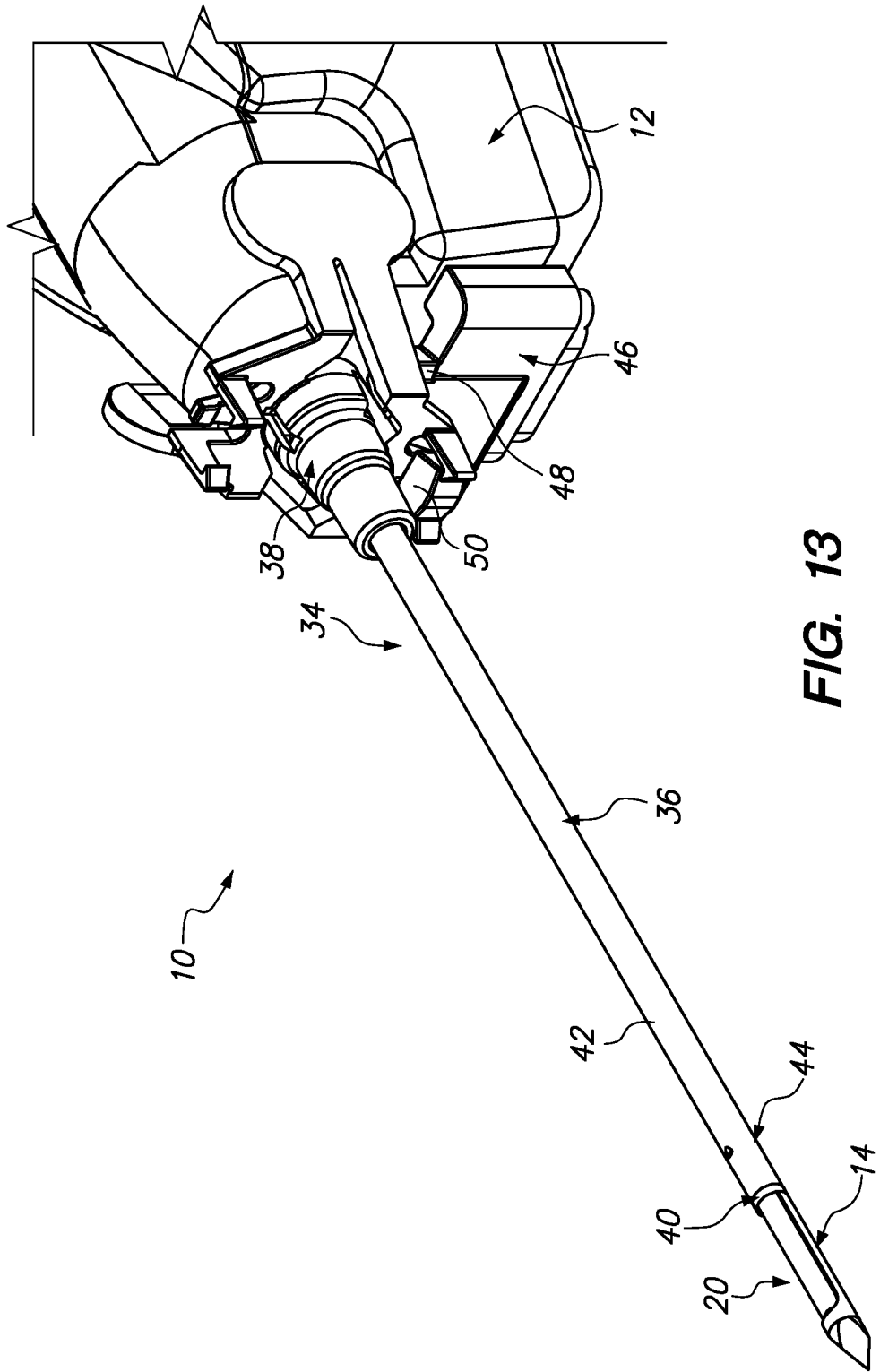
Figure 14:
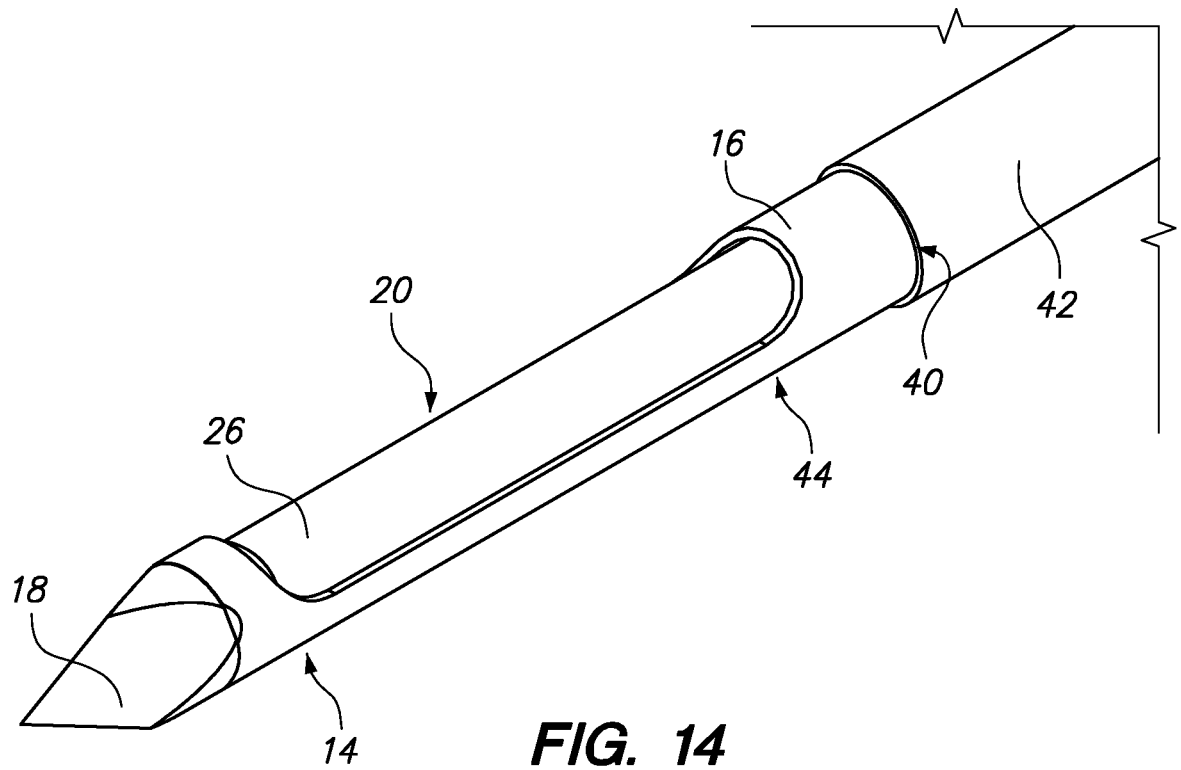
FIGS. 14 and 15 are perspective views of the inner and outer cannulas of the biopsy device, and the introducer depicted in FIGS. 12, 13, 16 and to 17. The introducer is coupled to the biopsy device in the standard configuration in FIG. 14. The introducer is coupled to the biopsy device in the petite configuration in FIG. 15.
Figure 15:
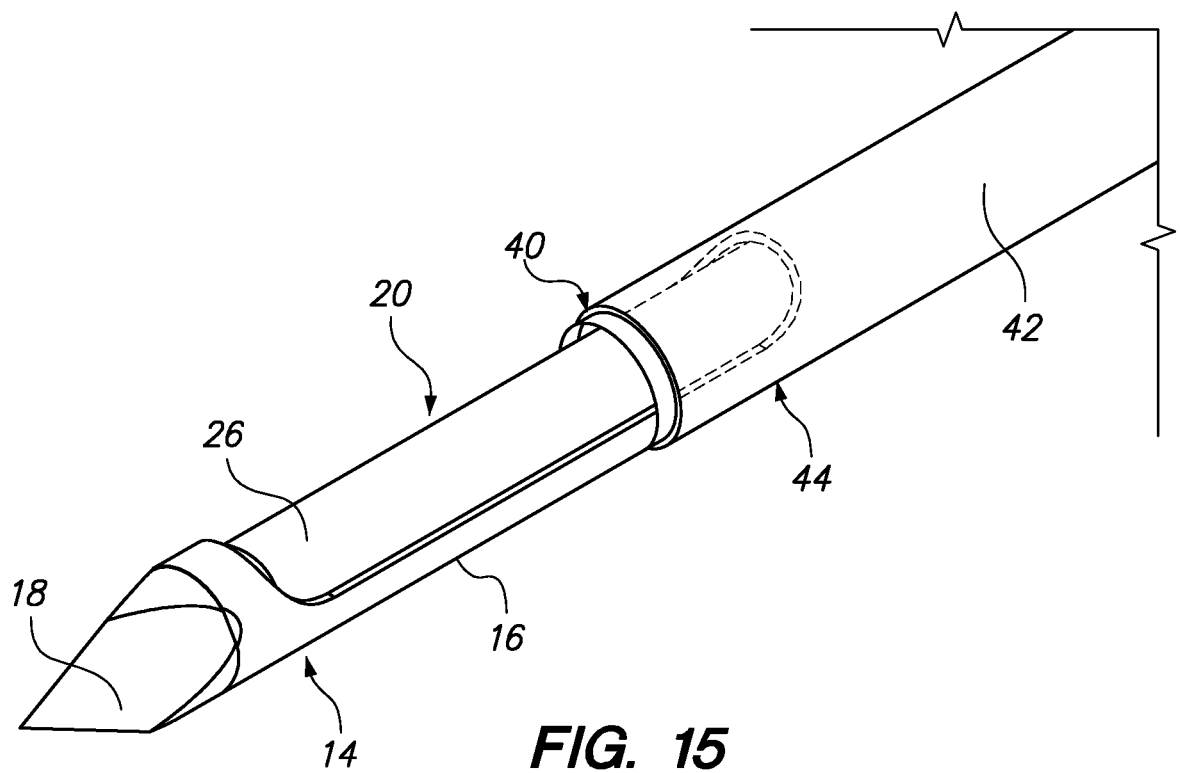
Figure 16:
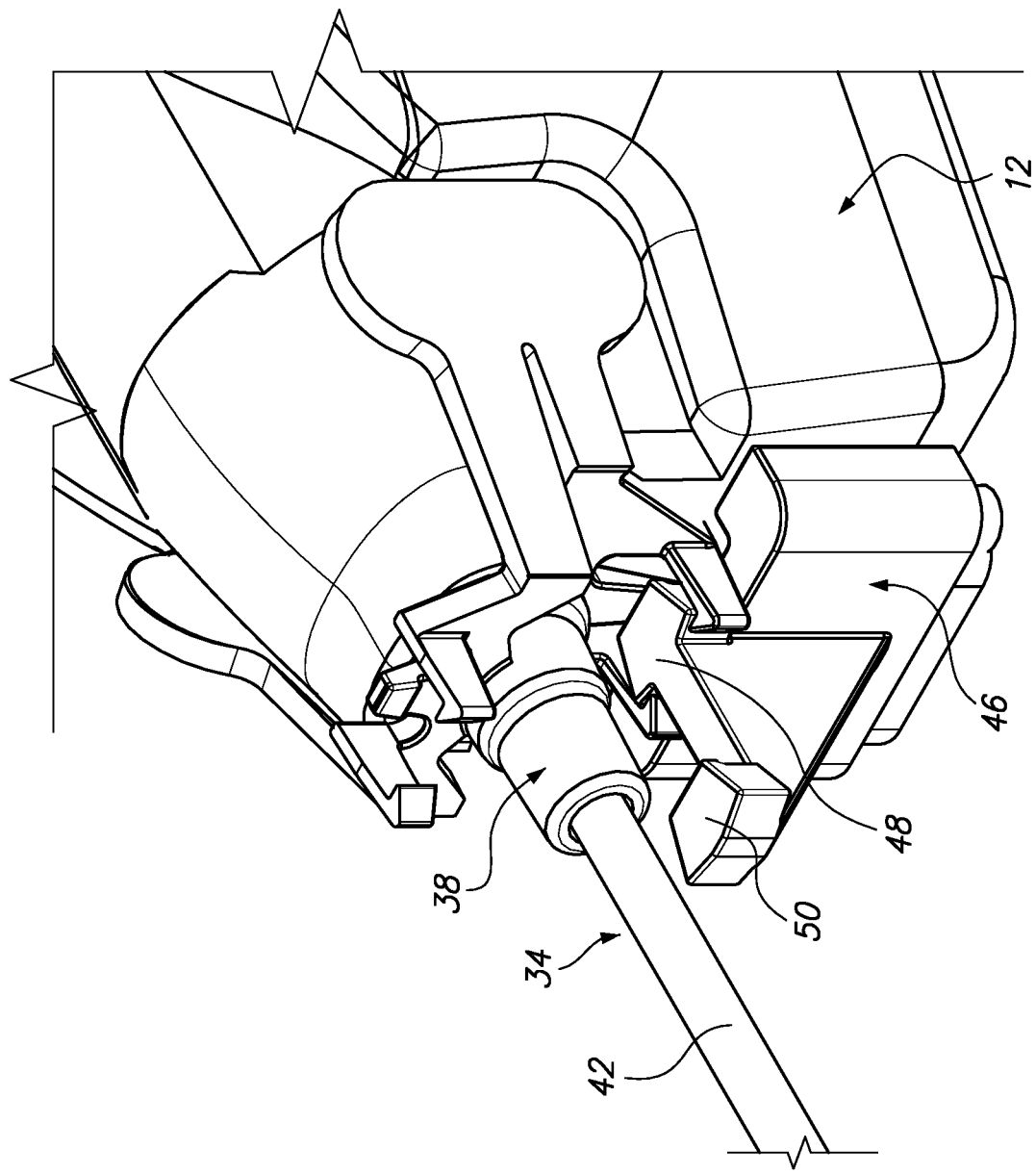

As shown in FIGS. 12 to 17, the introducer hub 38 is configured to couple the proximal end of the introducer 34 to a distal end of the body portion 12 of the biopsy device 10 in one of two positions. The distal tubular portion 42 of the introducer 34 is shown in phantom in FIGS. 12 to 17 for clarity. In FIGS. 12, 14 and 16, the introducer 34 is coupled to the body portion 12 of the biopsy device 10 in the "standard" position. In the standard configuration, the open distal end 40 of the introducer 34 is proximal of the tissue receiving aperture 20, as shown in FIG. 14. Therefore, the introducer 34 does not overlay or obscure any portion of the tissue receiving aperture 20. With the introducer 34 in the standard configuration, tissue receiving aperture 20 is in its full-size, e.g., 20 mm.

Figure 17:
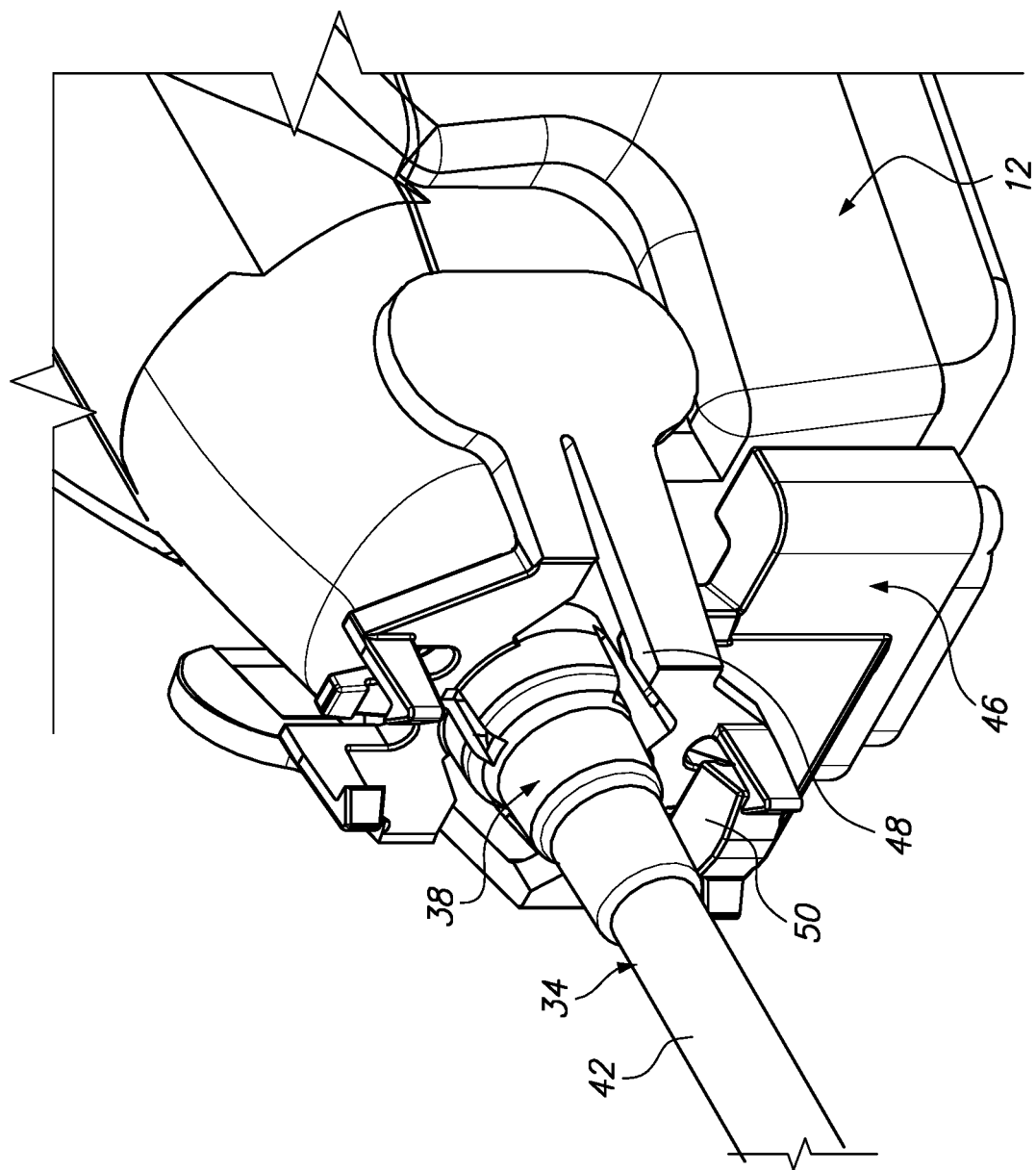
Figure 18:
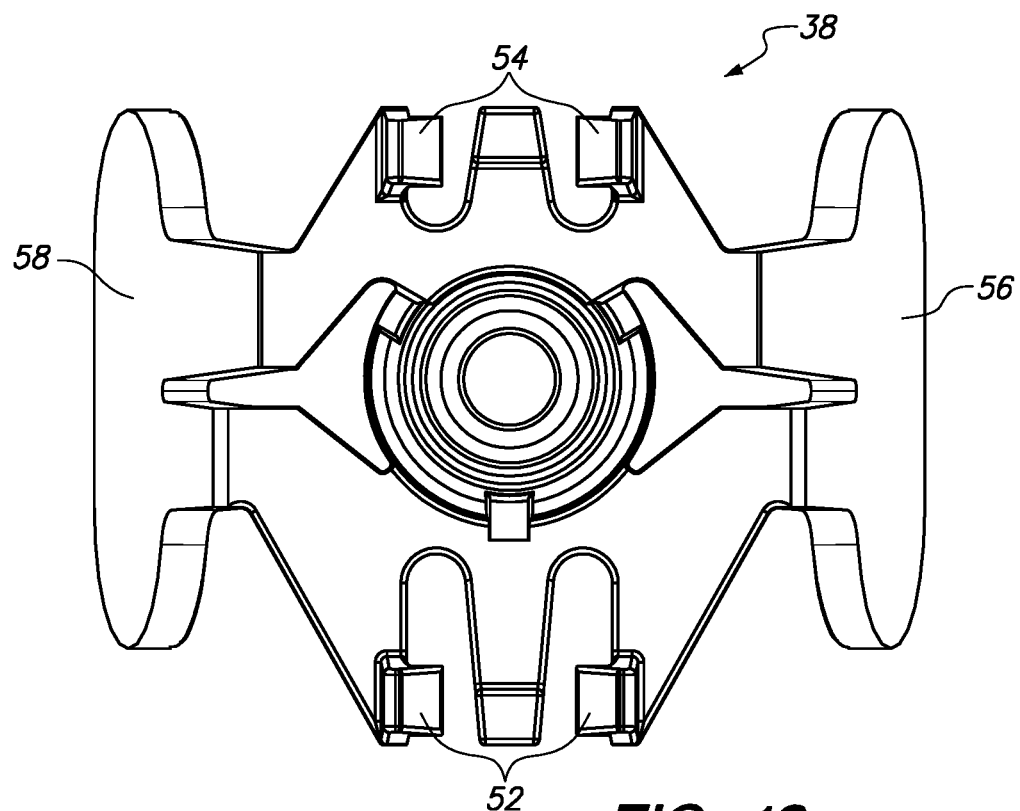
FIGS. 18 to 25 are various detailed perspective views of an introducer hub, according to one embodiment. The introducer hub is shown in phantom in FIGS. 22 and 23 for clarity.

In FIGS. 13, 15 and 17, the introducer 34 is coupled to the body portion 12 of the biopsy device 10 in the "petite" position. The introducer 34 can be transitioned between the standard and petite configurations by: (1) detaching the introducer 34 from the body portion 12; (2) rotating the introducer 34 on the outer cannula 16 by 180°; and (3) reattaching the introducer 34 to the body portion 12. In the petite configuration, the introducer 34 is mounted more distally on the outer cannula 16 compared to the standard configuration, as shown by comparing FIGS. 16 and 17. In the petite petition, a distal portion 40 of the introducer 34 overlays and obscures a proximal portion 44 of the tissue receiving aperture 20, thereby reducing the size of the tissue receiving aperture 20, as shown in FIG. 15. As a result, with the introducer 34 in the petite configuration, the tissue receiving aperture 20 has a reduced "petite" size, e.g., 12 mm.

As shown in FIGS. 1 to 7, 12, 13, 15 and 17, the biopsy device 10 is also configured to be coupled to an adapter 46 (also included in the biopsy system). The biopsy device 10 and the adapter 46 together form a support structure. The adapter 46 is in turn configured to be coupled to a stable surface, such as a stereotactic table (not shown), to stabilize the biopsy device 10 during a biopsy procedure. The adapter 46 includes proximal and distal detents 48, 50 (best shown in FIG. 2), which facilitate attachment of the introducer 34 to the tissue biopsy device 10 in the standard and petite configurations, respectively, as described below. Each detent 48, 50 defines a pair of laterally spaced apart detent latches. The distal detent 50 is located distal of the proximal detent 48. The distal detent 50 is also located above the proximal detent 48 (see FIG. 2).

FIGS. 18 to 25 illustrate the introducer hub 38 without the distal tubular portion 42 of the introducer 34. As seen in those figures, the introducer hub 38 includes respective pairs of standard and petite connector arms 52, 54 extending from the bottom and top of the introducer hub 38 when the introducer 34 is in the standard configuration. The standard arms 52 are laterally space apart from each other. Similarly, the petite arms 54 are laterally space apart from each other. The standard arms 52 are located proximal of the petite arms 54 (see FIG. 20). The axial distance between the standard and petite arms 52, 54 is about the same as the axial distance between the proximal and distal detents 48, 50. The standard arms 52 are configured to releasably couple to the proximal detent 48 on the adapter 46 to releasably couple the introducer 34 to the adapter 46 and the biopsy device 10 in the standard configuration (see e.g., FIG. 16). The petite arms 54 are configured to releasably couple to the distal detents 50 on the adapter 46 to releasably couple the introducer 34 to the adapter 46 and the biopsy device 10 in the petite configuration (see e.g., FIG. 17). As explained above, the introducer 34 can be transitioned between the standard and petite configurations the rotating 180° about the outer cannula 16. While the introducer 34 in this embodiment is attached to the biopsy device 10 via the adapter 46, in other embodiments, the introducer 34 may attach directly to the biopsy device 10.

Figure 19:
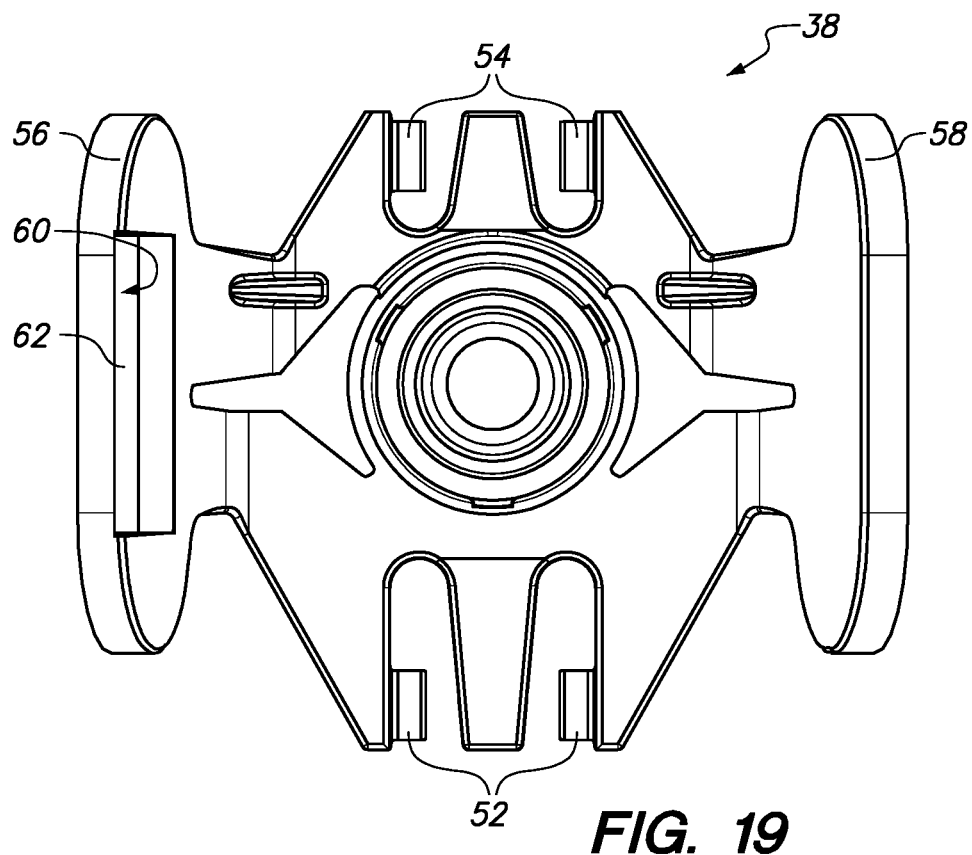
Figure 20:
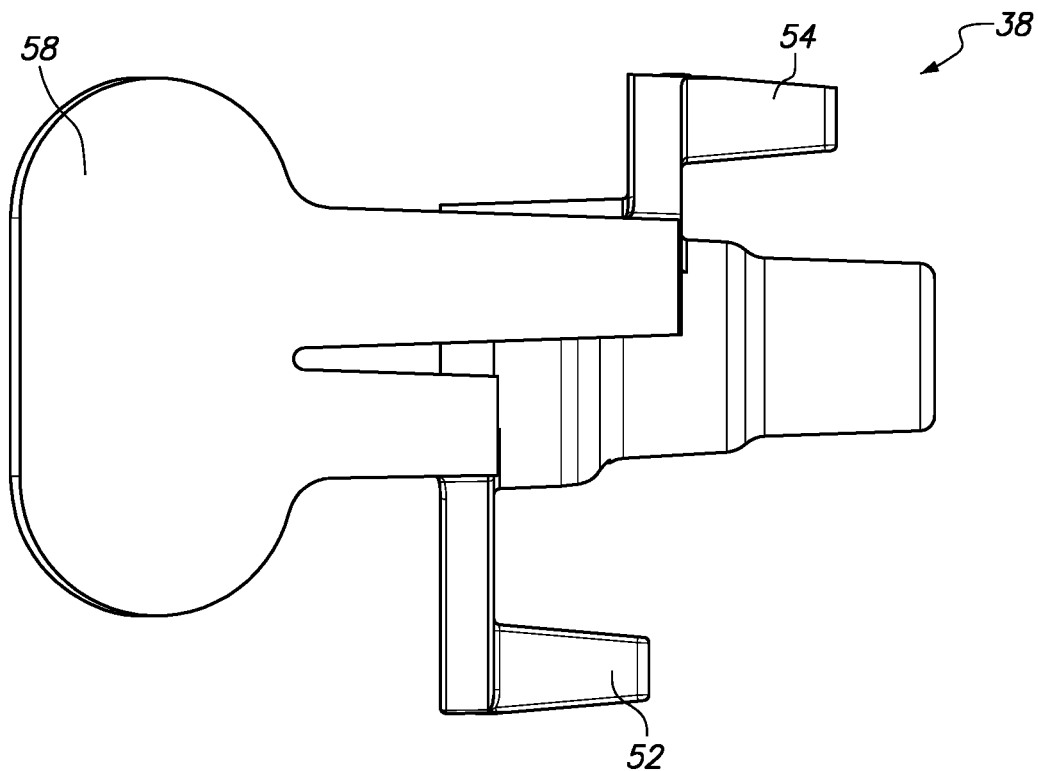
Figure 21:
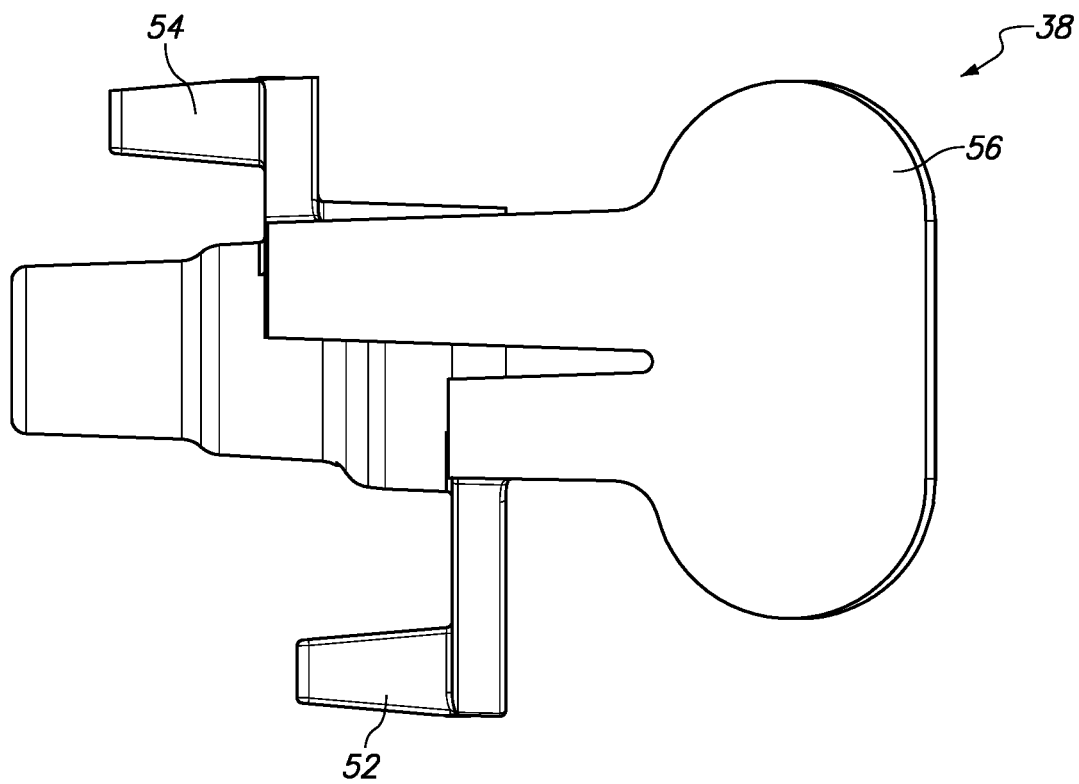
Figure 22:
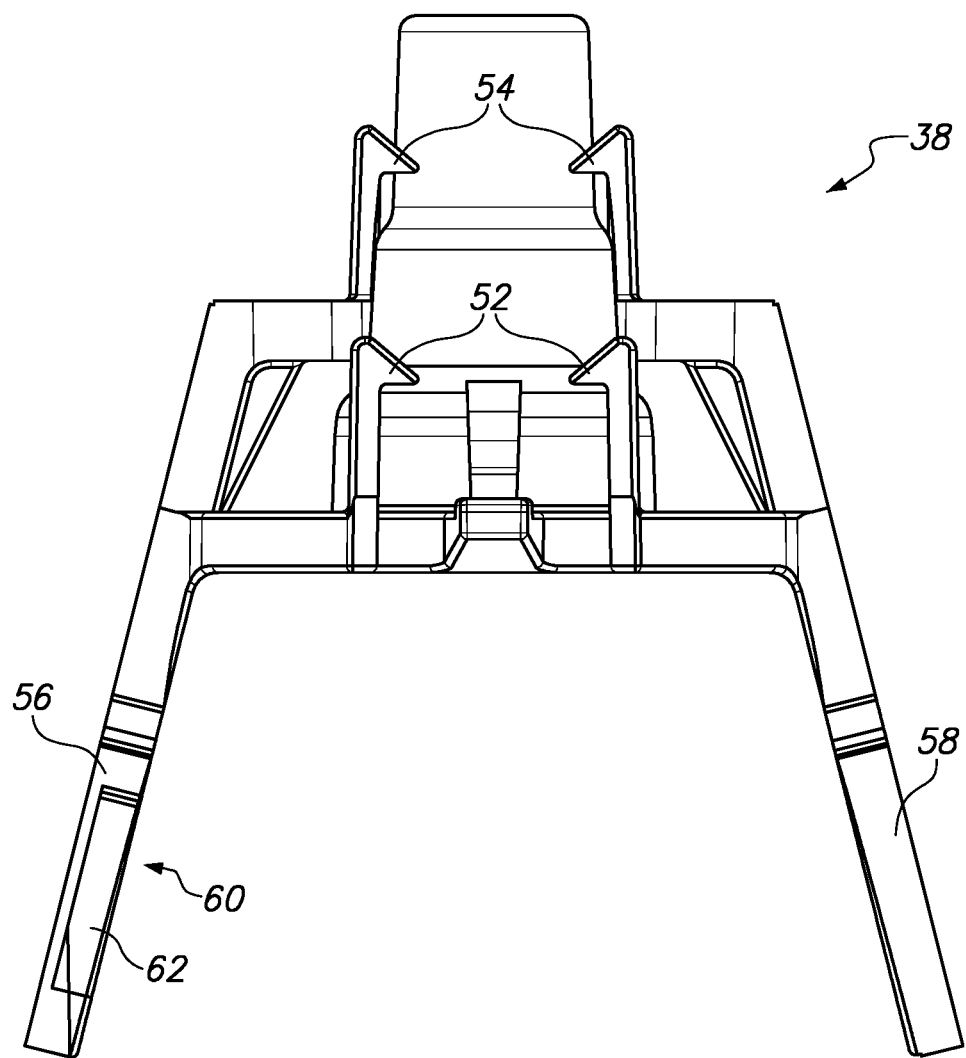
Figure 23:
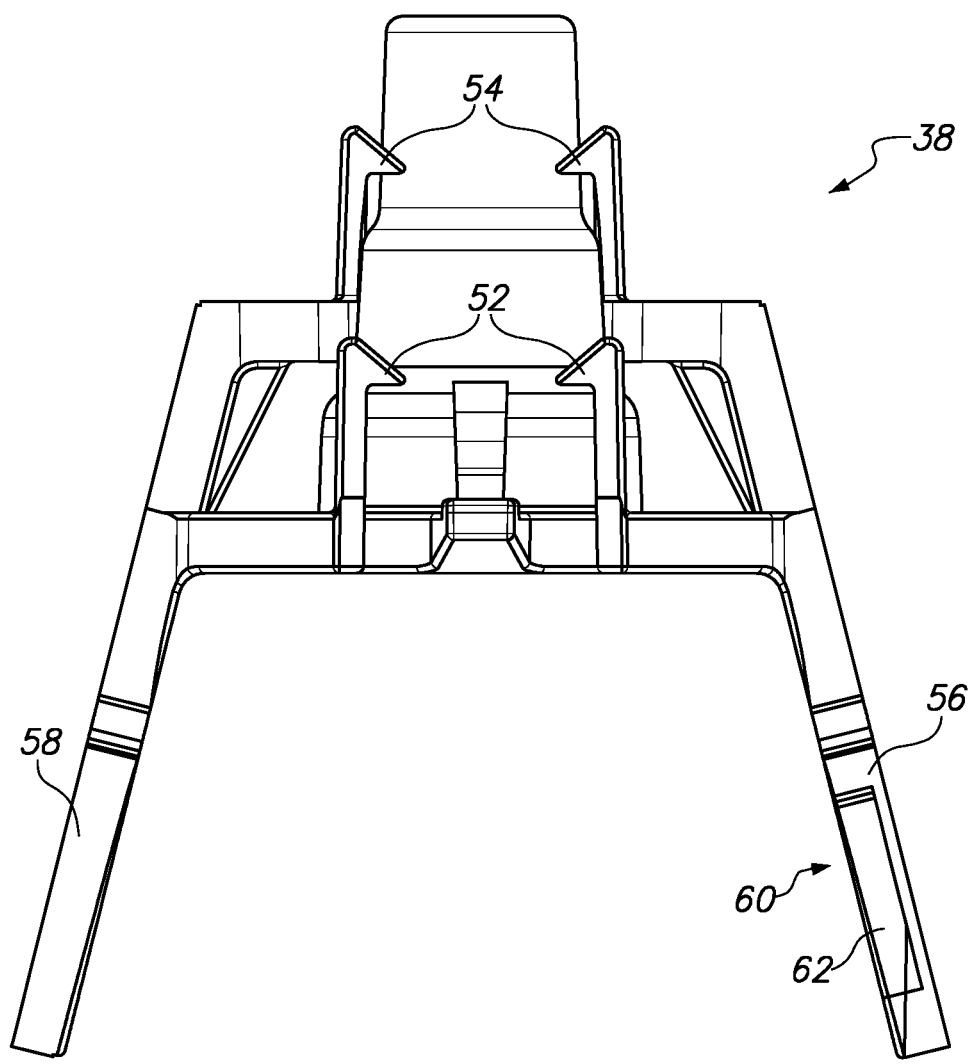
Figure 24:
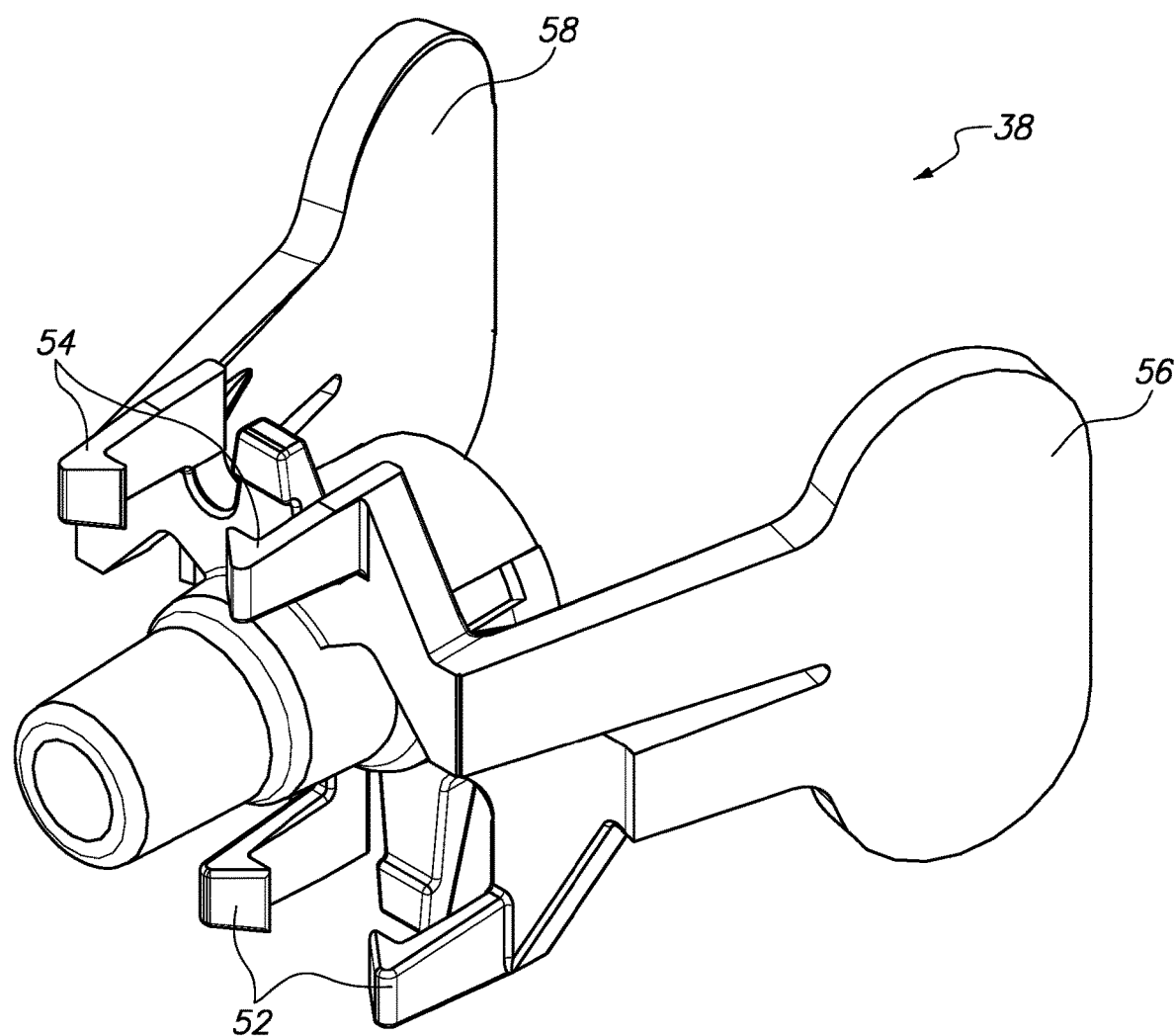
Figure 25:
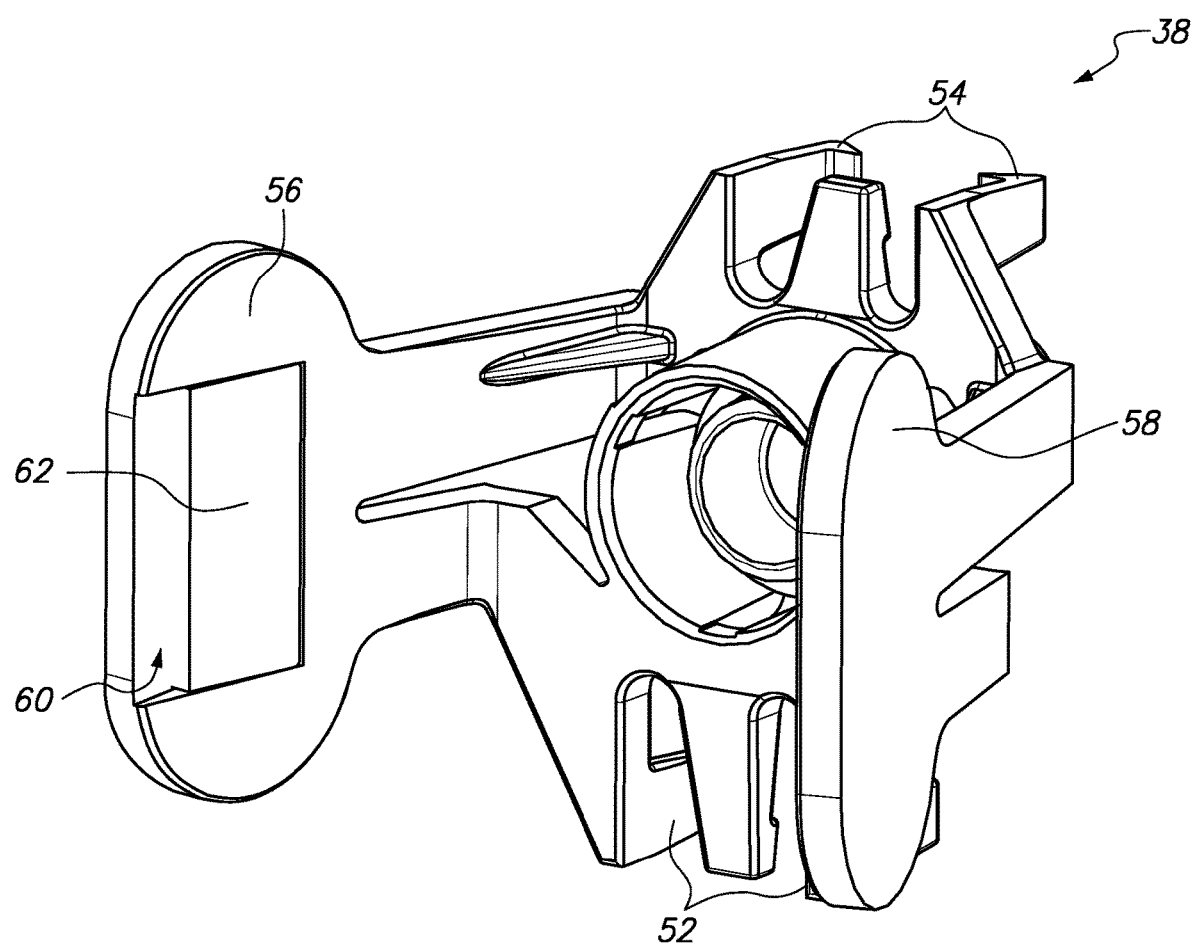

As shown in FIGS. 18 to 25, introducer hub 38 also includes left and right tabs 56, 58. The directional terms left and right are from the perspective of the user, behind the introducer hub 38, when the introducer 34 is coupled to the body portion 12 of the biopsy device 10 in the standard configuration, as shown in FIG. 19. The left tab 56 includes a recess 60 (best shown in FIG. 19) in which a sensor detectable locating element 62, e.g., a magnet, is fixedly coupled to the left tab 56. The locating element 62 is configured to be detected by two sensors 64, 66 in a distal end of the body portion 12 of the biopsy device 10, as described below. For instance, the sensors 64, 66 can be Hall Effect sensors if the locating element 62 is a magnet. The tabs 56, 58 can be squeezed together to open the standard and petite arms 52, 54 to remove the introducer 34 from the adapter 46. The sensors 64, 66 are laterally spaced apart from each other on respective left and right sides of the body portion 12 of the biopsy device 10. The sensors 64, 66 are also axially spaced apart from each other as described below.

FIGS. 26 to 32 depict the interaction between the locating element 62 in the left tab 56 of the introducer hub 38 and the sensors 64, 66 in the body portion 12 of the biopsy device 10. FIGS. 26 to 31 depict the body portion 12 of the biopsy device 10 with certain components omitted and the housing shown in phantom to allow visualization of the left and right sensors 64, 66 (best seen in FIGS. 26 and 29, respectively).

Figure 26:
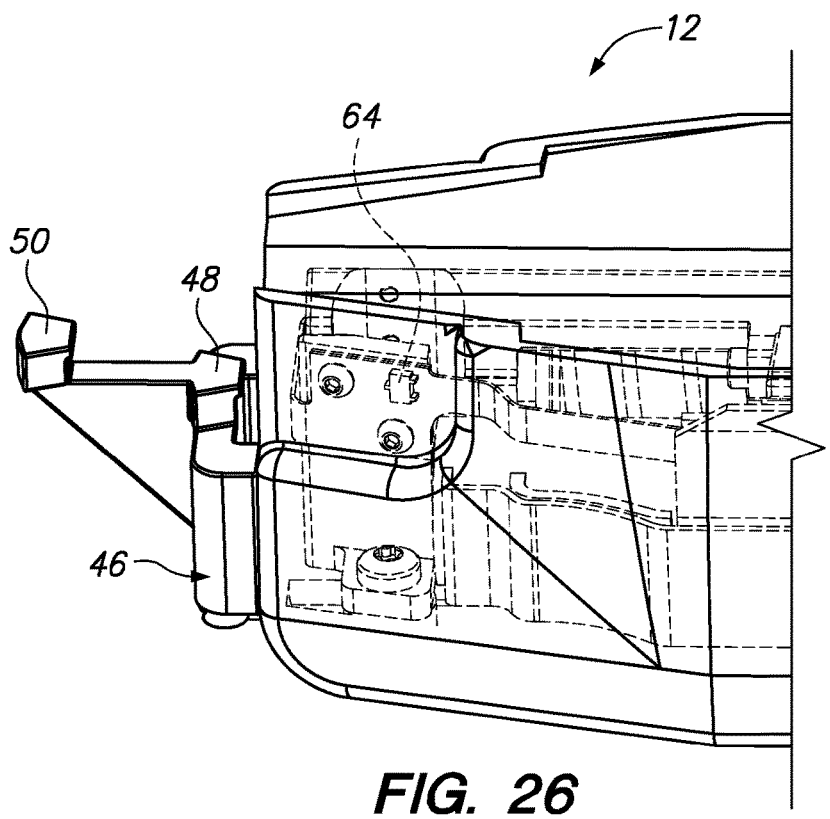
FIGS. 26 and 29 are respective left and right detailed perspective views of a biopsy device and an adapter of a biopsy system, according to one embodiment. Various components of the biopsy device are omitted and the housing is shown in phantom for clarity and to allow visualization of the left and right sensors, respectively.
Figure 27:
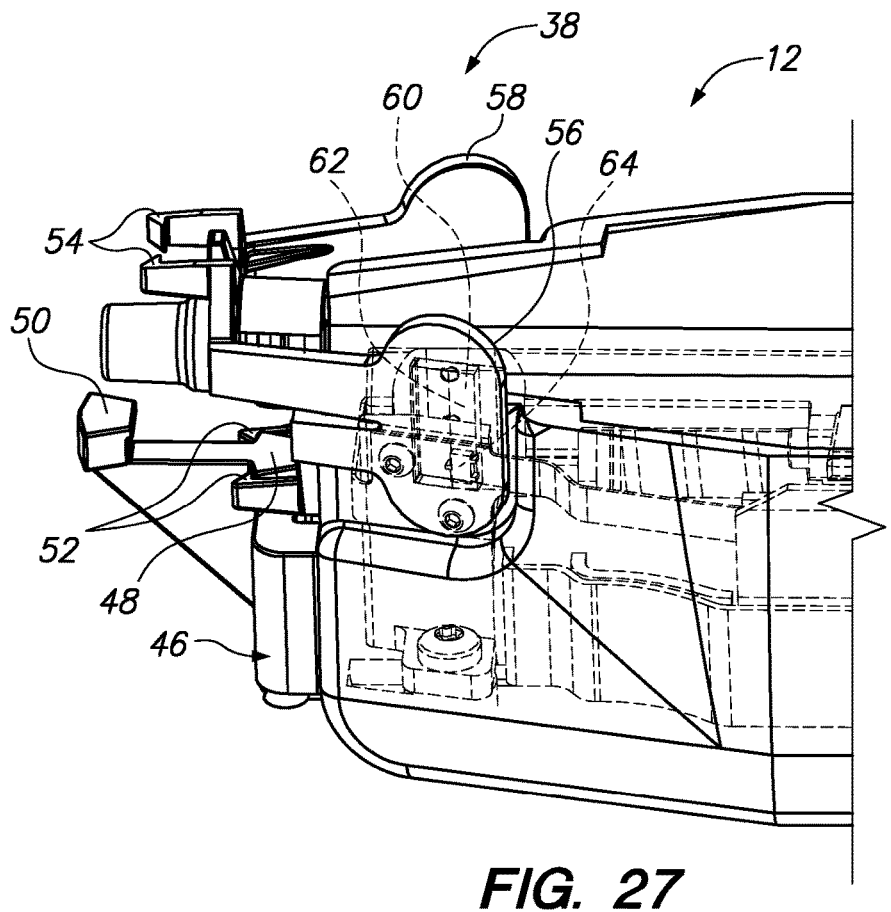
FIGS. 27 and 28 are respective left and right detailed perspective views of the biopsy device and adapter depicted in FIGS. 26 and 29 with an introducer attached thereto in the standard configuration. Various components of the biopsy device and the introducer are omitted and the housing is shown in phantom for clarity and to allow visualization of the left and right sensors, respectively.
Figure 28:
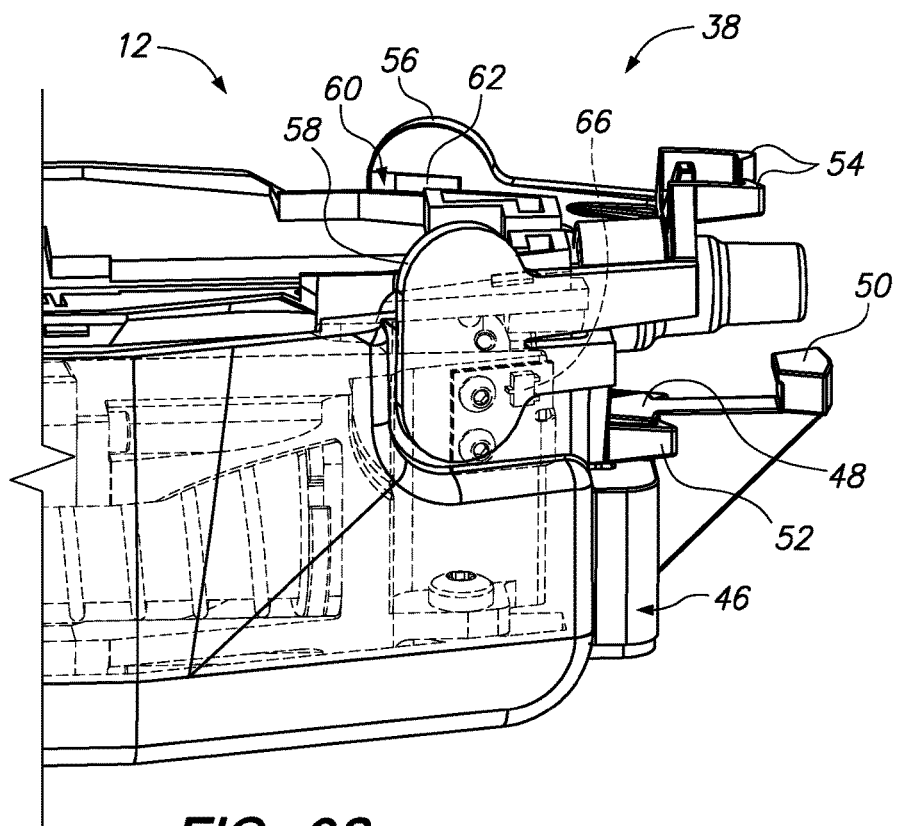
Figure 29:
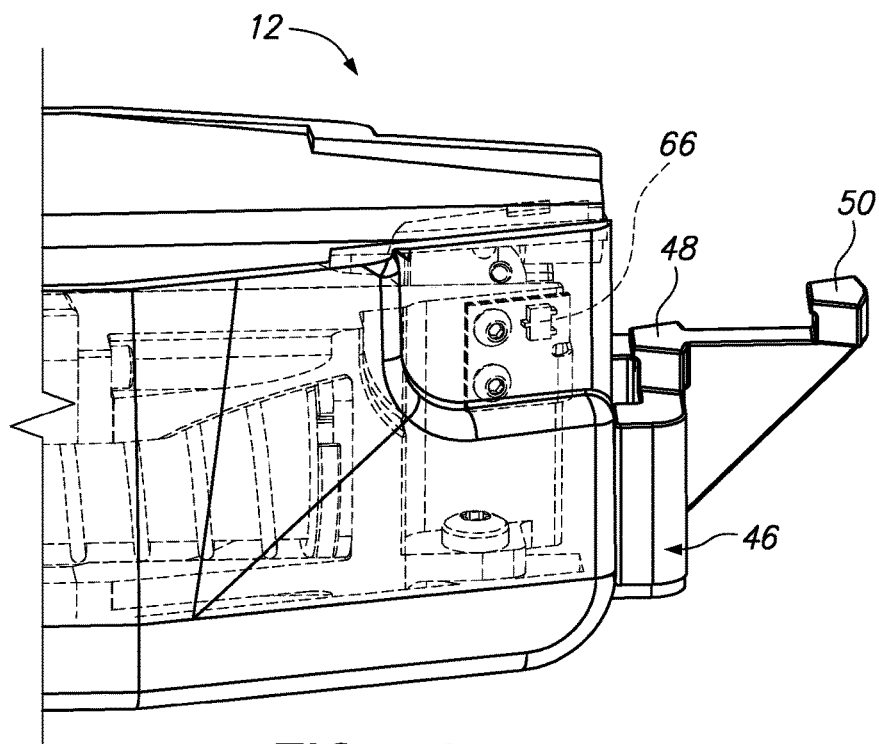
Figure 32:
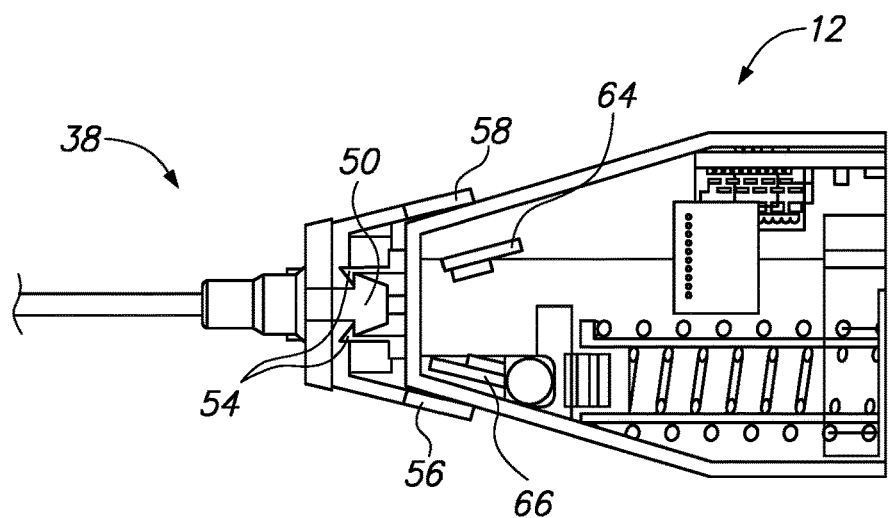
FIG. 32 is a bottom cross-sectional view of a biopsy device of a biopsy system with an introducer attached thereto in the petite configuration, according to one embodiment.

The left sensor 64 is located more proximally in the body portion 12 compared to the right sensor 66, as shown in FIGS. 26, 29 and 32. The axial position of the left sensor 64 corresponds to the axial position of the left tab 56 when the introducer 34 is coupled to the body portion 12 of the biopsy device 10 in the standard configuration. As such, when the introducer 34 is coupled to the body portion 12 of the biopsy device 10 in the standard configuration, the locating element 62 is not only disposed on the left side of the biopsy device 10, wherein the left sensor 64 is located, but the locating element 62 is also disposed axially adjacent the left sensor 64, as shown in FIG. 27. On the other hand, the locating element 62 is disposed on the other side of the body portion 12 of the biopsy device 10 from the right sensor 66, as shown in FIG. 28. Therefore, when the introducer 34 is in the standard configuration, the left sensor 64 detects the proximity of the locating element 62, and the right sensor 66 does not detect the proximity of the locating element 62. The sensors 64, 66 send respective signals to the controller in the biopsy device 10.

Figure 30:
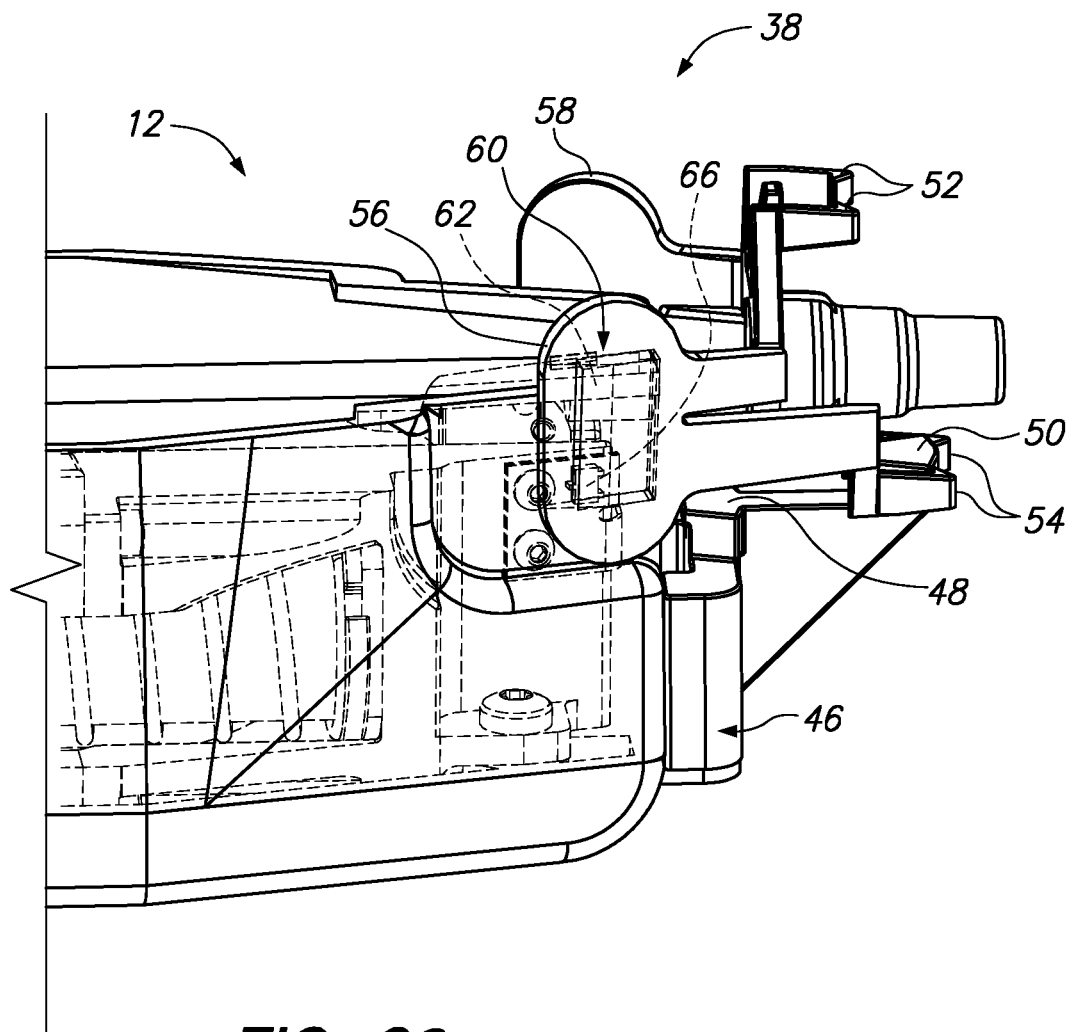
FIGS. 30 and 31 are respective left and right detailed perspective views of the biopsy device and adapter depicted in FIGS. 26 and 29 with an introducer attached thereto in the petite configuration. Various components of the biopsy device and the introducer are omitted and the housing is shown in phantom for clarity and to allow visualization of the left and right sensors, respectively.
Figure 31:
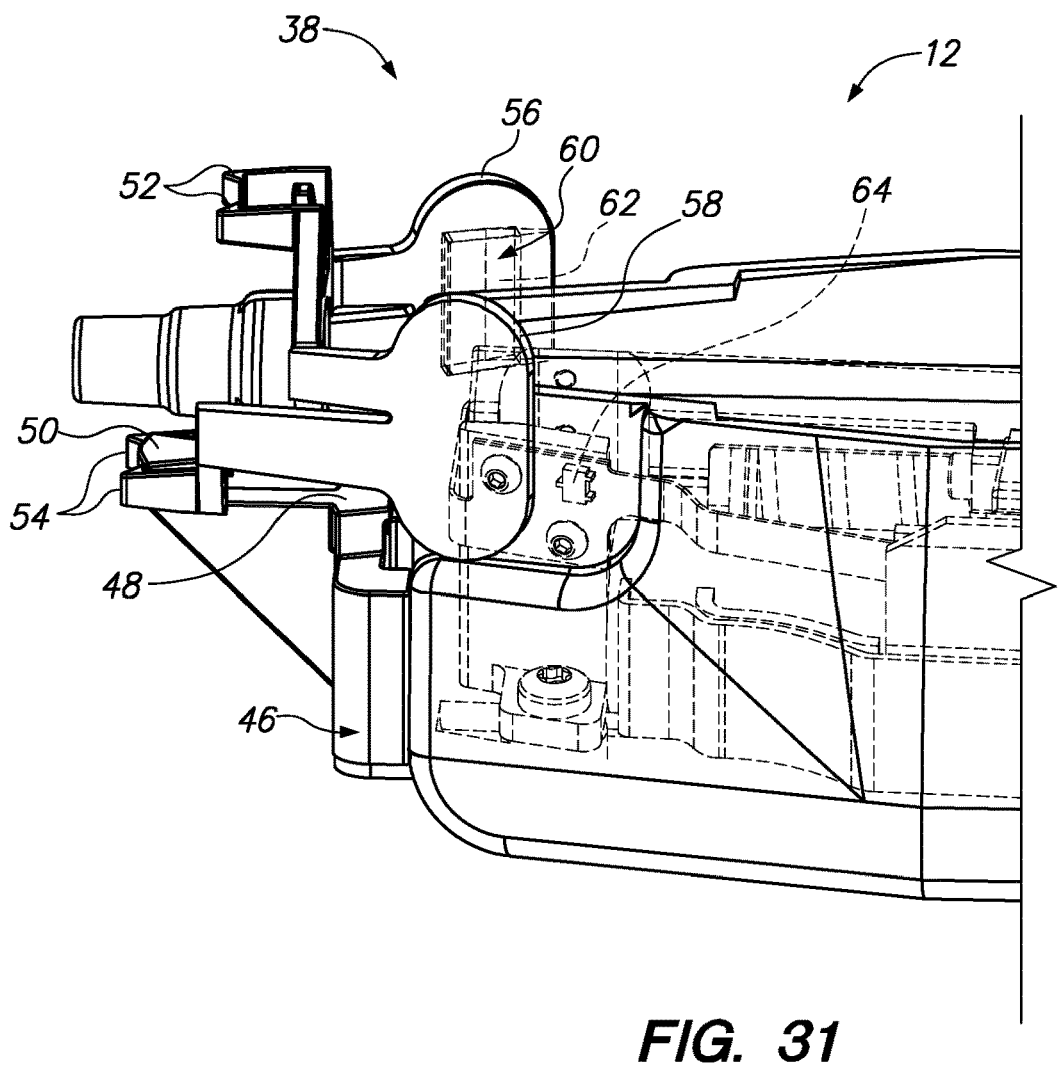

The right sensor 66 is located more distally in the body portion 12 compared to the left sensor 64, as shown in FIGS. 26, 29 and 32. The axial position of the right sensor 66 corresponds to the axial position of the left tab 56 when the introducer 34 is coupled to the body portion 12 of the biopsy device 10 in the petite configuration. As such, when the introducer 34 is coupled to the body portion 12 of the biopsy device 10 in the petite configuration, the locating element 62 is not only disposed on the right side of the biopsy device 10, wherein the right sensor 66 is located, but the locating element 62 is also disposed axially adjacent the right sensor 66, as shown in FIG. 30. On the other hand, the locating element 62 is disposed on the other side of the body portion 12 of the biopsy device 10 from the left sensor 64, as shown in FIG. 31. Therefore, when the introducer 34 is in the petite configuration, the right sensor 66 detects the proximity of the locating element 62, and the left sensor 64 does not detect the proximity of the locating element 62. The sensors 64, 66 send respective signals to the controller in the biopsy device 10.

The controller is configured to receive the signals from the left and/or right sensors 64, 66, which represent location data of the locating element 62, and to analyze the signals to determine whether the introducer 34 has been coupled to the biopsy device 10 in the standard or petite configuration. When the locating element 62 is in a proximal position adjacent the left sensor 64, the controller determines that the introducer 34 is coupled the biopsy device 10 in the standard configuration. In response to that determination, the controller instructs the drive assembly to move (i.e., axially oscillate) the inner cannula 26 through a standard (oscillation) stroke length, e.g., 23 mm. When the locating element 62 is in a distal position adjacent the right sensor 66, the controller determines that the introducer 34 is coupled to the biopsy device 10 in the petite configuration. In response that determination, the controller instructs to drive assembly to move the inner cannula 26 through a petite stroke length, e.g., 15 mm. In this manner, the orientation and location of the introducer hub 38, and therefore the locating element 62, relative to the left and right sensors 64, 66 in the biopsy device 10 automatically determines the stroke length of the inner cannula 26. Exemplary mechanisms for adjusting the stroke length of the inner cannula 26 are described in U.S. Provisional Patent Application Ser. No. 62/055,610, which was incorporated by reference above. If neither of the left or right sensors 64, 66 detect an adjacent locating element 62, they send respective signals to the controller. The controller interprets those signals as indicating the lack of a properly installed introducer 34, and halts the biopsy procedure.

Alternatively or additionally, signals from the left and/or right sensors 64, 66 (indicating the standard or petite configuration of the introducer 34) can cause the controller to instruct the drive mechanism to change the distance the outer and inner cannulas 16, 26 are fired into tissue at the beginning of a biopsy procedure. When the introducer 34 is coupled to the biopsy device 10 in the petite configuration, the outer and inner cannulas 16, 26 are retracted and fired a shorter distance than when the introducer 34 is in the standard configuration. Exemplary mechanisms for adjusting the firing distance of the outer and inner cannulas 16, 26 (between a proximal armed position and a distal fired position) are described in U.S. Provisional Patent Application Ser. No. 62/055,610, which was incorporated by reference above. Retracting and firing the outer and inner cannulas 16, 26 a shorter distance allows the user to insert the tissue piercing tip 20 of the armed outer cannula 18 a short distance through the skin and into a petite breast while minimizing the possibility that the tissue piercing tip 20 of the outer cannula 18 will be fired through the breast tissue into which it was pre-inserted before firing, as described in U.S. Provisional Patent Application Ser. No. 62/055,610. Firing a pre-inserted outer cannula 16, in turn, improves accuracy and reduces tissue damage.

Figure 33:
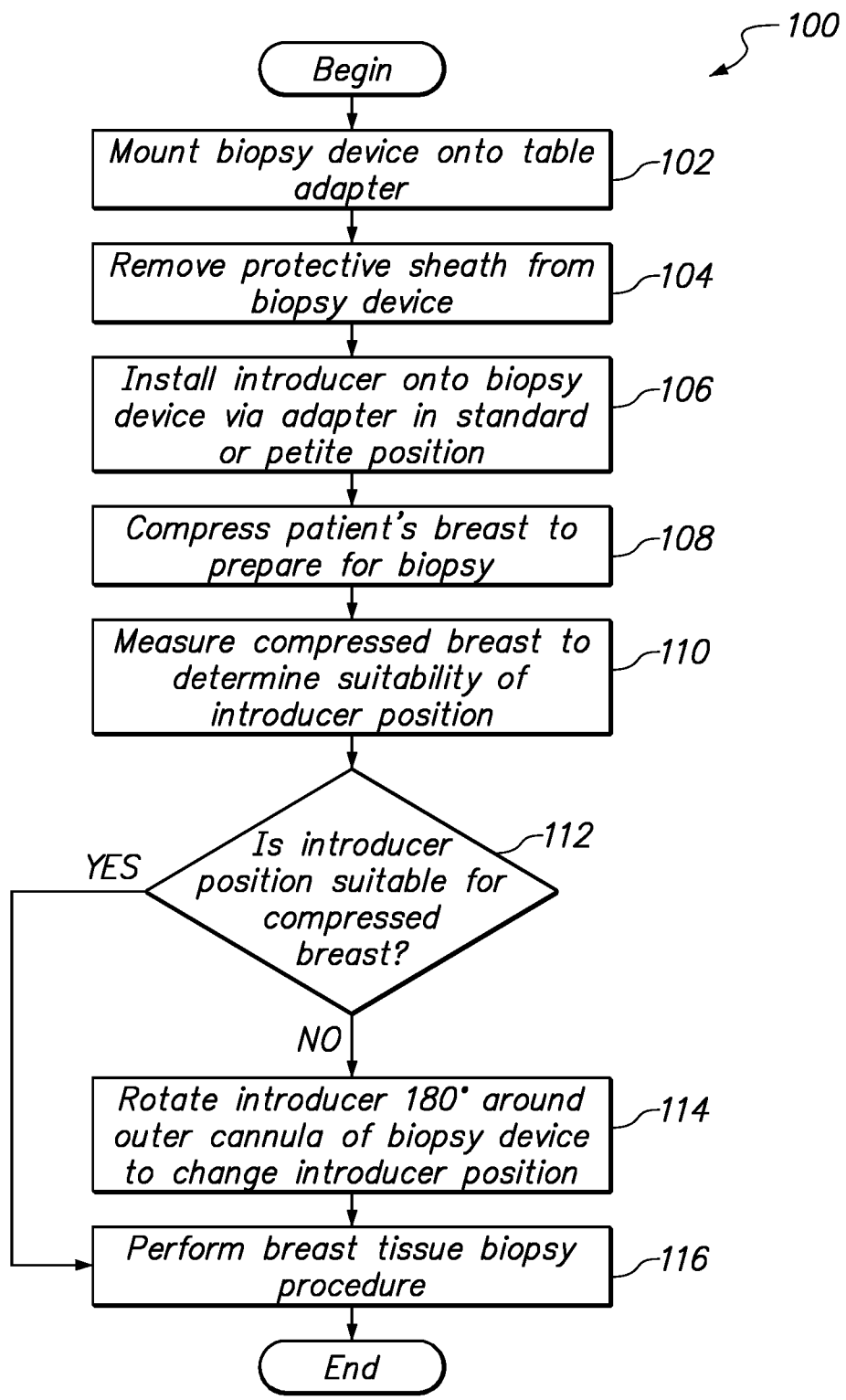
FIG. 33 is a flow-chart depicting a breast biopsy procedure, according to one embodiment.
Figure 34:
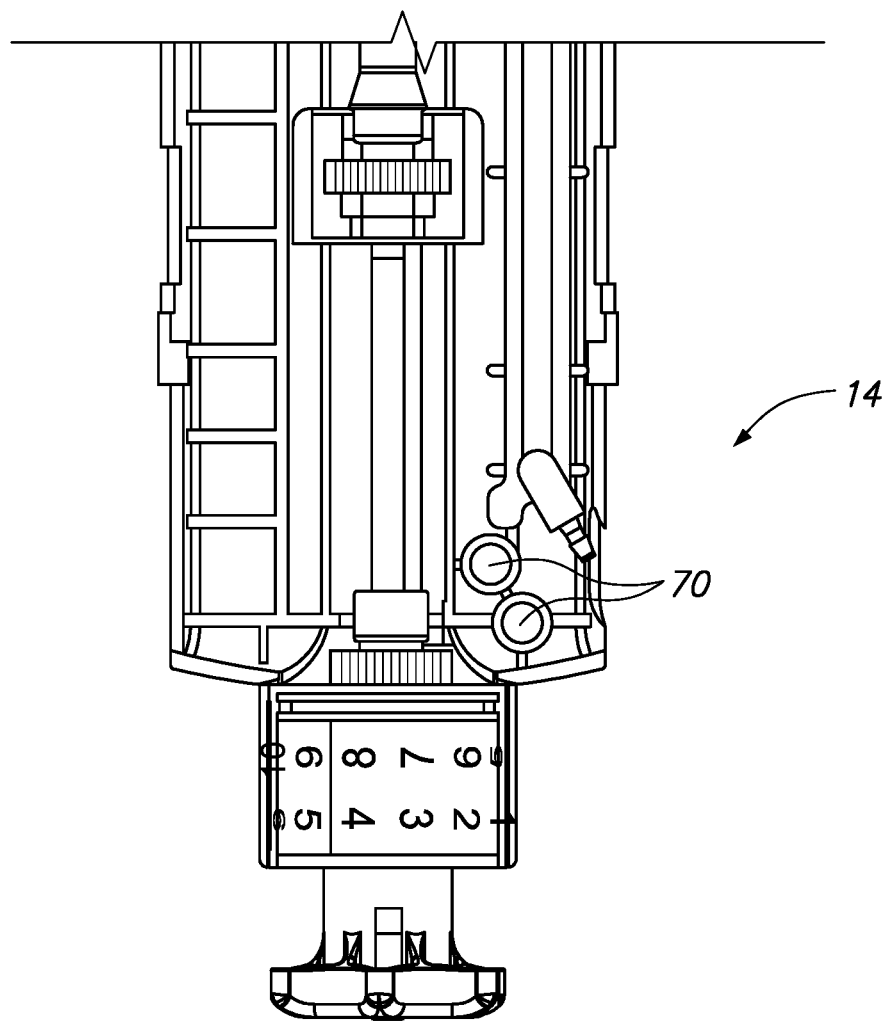
FIG. 34 is a detailed bottom view of a needle portion of a biopsy device of a biopsy system with certain components omitted for clarity and to allow visualization of the two sensor detectable needle portion elements therein.

Having described the structure of various components of the biopsy device 10, the adapter 46 and the introducer 34, a breast biopsy procedure 100 using the biopsy device 10, the adapter 46 and the introducer will now be described. FIG. 33 depicts the steps of a breast biopsy procedure 100 according to one embodiment. At step 102, a user (e.g., a physician and/or a technician working under the direction of a physician) mounts the biopsy device 10 to the adapter 46, which is in turn coupled to a stable surface like a stereotactic surgical table. At step 104, the user removes a protective sheath from the biopsy device 10. The protective sheath protects the biopsy device 10 and maintains sterility during shipping and storage. The protective sheath may cover only the needle portion 14 of the biopsy device 10, which will be inserted into the patient.

At step 106, the user installs the introducer 34 onto the biopsy device 10 via the adapter 46. As discussed above, in other embodiments, the introducer 34 may be coupled to the biopsy device 10 without coupling to the adapter 46. The user can install the introducer 34 in either the standard or petite configuration based on the patient's history or anatomy. At step 108, the user compresses the patient's breast to prepare for the breast tissue biopsy. At step 110, the user measures the compressed breast. At step 112, the user determines whether the introducer position (and the corresponding tissue receiving aperture size and stroke length) is suitable for the compressed breast.

If the introducer position is suitable, the user performs the breast tissue biopsy procedure 100 at step 116. Performing the procedure 100 can include initiating a computer controlled procedure. If the introducer position is not suitable, the user rotates the introducer 34 180° around the outer cannula 16 to change to the alternate introducer position at step 114. In detail, the user first uncouples the introducer hub 38 from the adapter 46 without removing the introducer 34 from the outer cannula 16. Next, the user rotates the introducer 34 180° around the outer cannula 16. Finally, the user recouples the introducer hub 38 to the adapter 46 with the introducer 34 in the alternate introducer position (e.g., from standard to petite). Because the introducer remains slidably and rotatably mounted to the introducer 34 during step 114, introducer position can be changed with minimum effort and in a minimum amount of time, while minimizing the probability of contaminating the outer cannula 16. After the changing introducer position at step 114, the user performs the breast tissue biopsy procedure 100 at step 116, as described above. During the breast tissue biopsy procedure 100, the locating element 62 and the left and right sensors 64, 66 interact to automatically adjust the stroke length to match the aperture size resulting from the introducer position.

Although the procedure 100 depicted in FIG. 33 is a breast biopsy procedure, the disclosed biopsy device 10 and introducer 34 are suitable for any biopsy procedure that can be including a variable aperture size and stroke length. Similarly, while the introducer 34 is described as having two positions (i.e., standard and petite), the disclosed introducer 34 and locating element 62 are suitable for biopsy procedures with any number of aperture sizes, including a continuously adjustable aperture size. In such embodiments, the locating element 62 can be configured to interact with one or more sensors configured to determine the longitudinal, axial or rotational position of the locating element 62. In response to signals from the one or more sensors, the controller in the biopsy device varies the stroke length to match the aperture.

Figure 35:
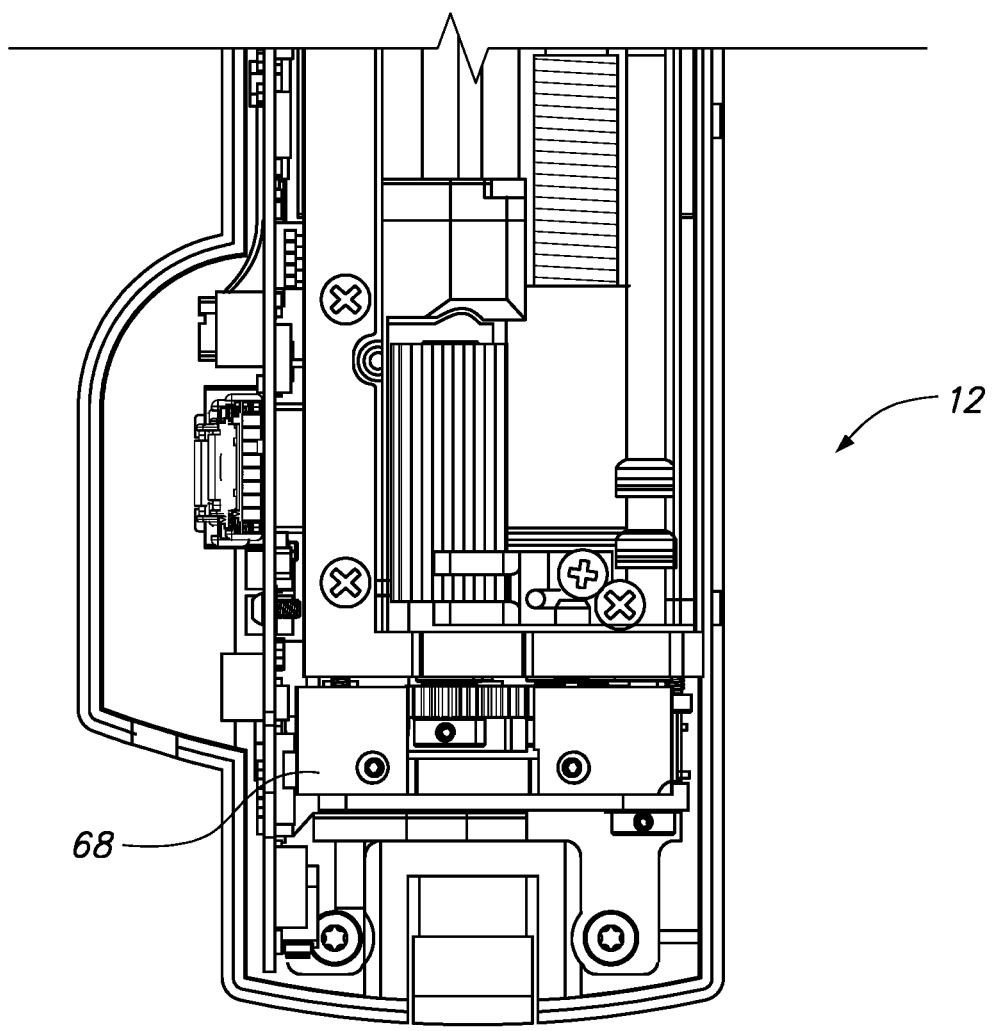
FIG. 35 is a detailed top view of a body portion of a biopsy device of a biopsy system with certain components omitted for clarity and to allow visualization of the needle portion sensor therein.

Although the sensors 64, 66 described herein are configured to detect a position of the introducer 34. Similar sensors can be used to detect other aspects of the biopsy device 10 and to report same to the controller therein. For instance, FIG. 35 depict a needle portion sensor 68 (e.g., a Hall Effect sensor) in the body portion 12 of the biopsy device 10. The needle portion sensor 68 is configured to detect sensor detectable needle portion elements 70 (e.g., magnets) in the needle portion 14 of the biopsy device 10 to determine when a certain type of needle portion 14 (containing a certain type of outer cannula 16) has been attached to the body portion 12. When two sensor detectable needle portion elements 70 are detected by the needle portion sensor 68, the needle portion sensor 68 communicates with the controller for the biopsy device to confirm proximity of a needle portion 14 including an outer cannula 16 having a tissue piercing tip 18. When only one sensor detectable needle portion element 70 is detected by the needle portion sensor 68, the needle portion sensor 68 communicates with the controller for the biopsy device to confirm proximity of a needle portion 14 including an outer cannula 16 having a blunt tip. When no sensor detectable needle portion elements 70 are detected by the needle portion sensor 68, the needle portion sensor 68 communicates with the controller for the biopsy device to confirm the lack of a needle portion 14 in proximity to the body portion 12.

Instead of being fired into tissue, blunt outer cannulas are inserted into openings pre-formed in the tissue. Firing blunt outer cannulas can injure the patient and damage the biopsy device. Accordingly, upon detecting the only one sensor detectable needle portion element 70, the needle portion sensor 68 communicates with the controller, which then disables the firing mechanism in the biopsy device 10. Alternatively, the needle portion sensor 68 can detect two sensor detectable needle portion elements 70 in the needle portion 14 with a sharp outer cannula, and communicate with the controller to enable the firing mechanism. When the needle portion sensor 68 detects no sensor detectable needle portion elements 70 in its proximity, the needle portion sensor 68 communicates with the controller, which then disables the biopsy device 10.

While the sensors 64, 66 and locating element 62 in the above-described embodiments are Hall Effect sensors and magnets, other embodiments include optical beam break sensors and protruding sensor detectable elements that break the optical beams. While such sensors are binary, the biopsy device can be associated with more than one sensor to enable encoding of more than two states. Given "n" sensors, the number of states that can be identified is $2^n$.

FIGS. 36 to 44 depict a new, original and ornamental design for a needle portion of a two-part biopsy device for use as part of a medical diagnostic or treatment system.

Figure 36:
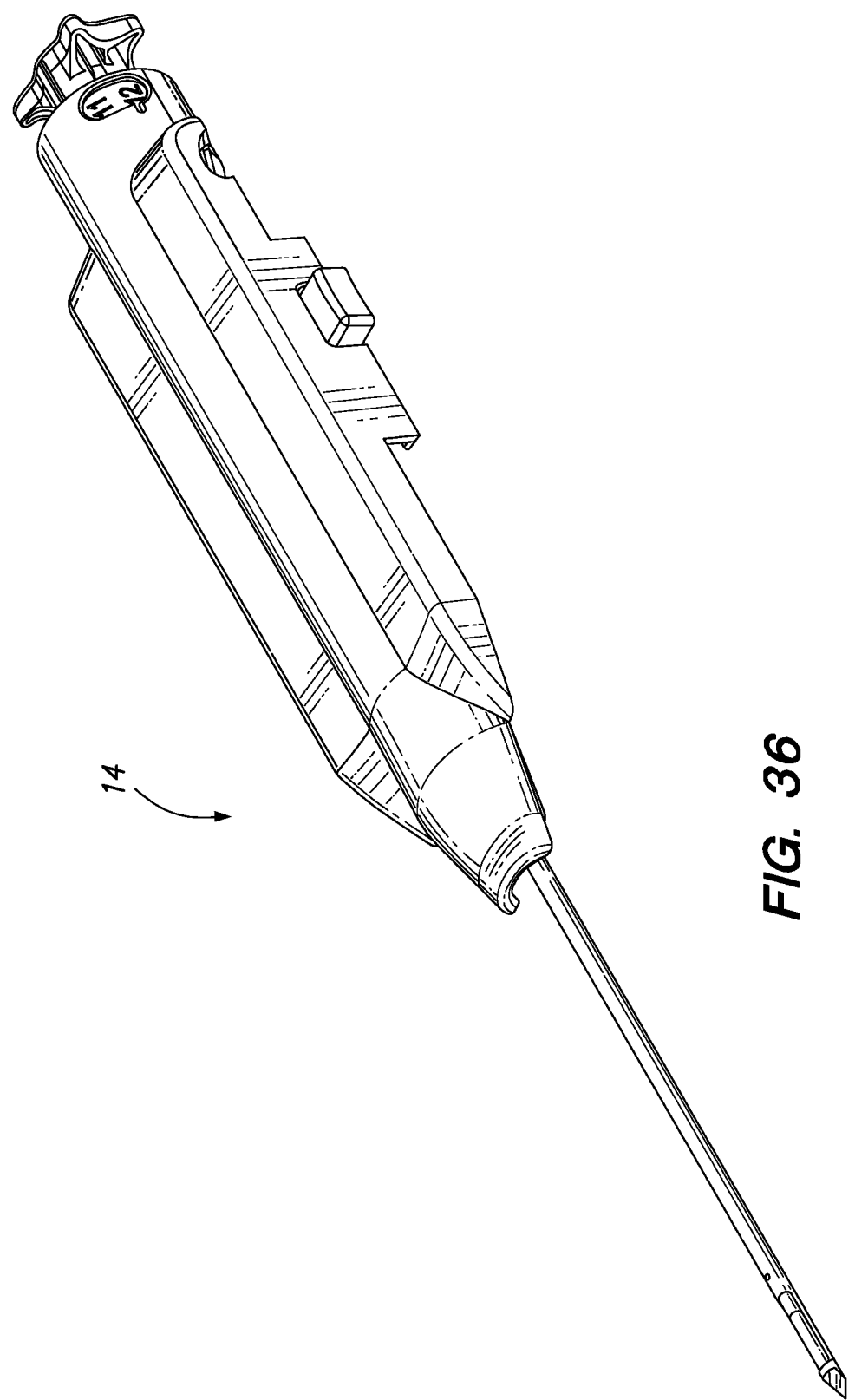
FIG. 36 is a perspective view of an embodiment of a needle portion of a two-part biopsy device.

FIG. 36 is a perspective view of an embodiment of a needle portion of a two-part biopsy device.

Figure 37:
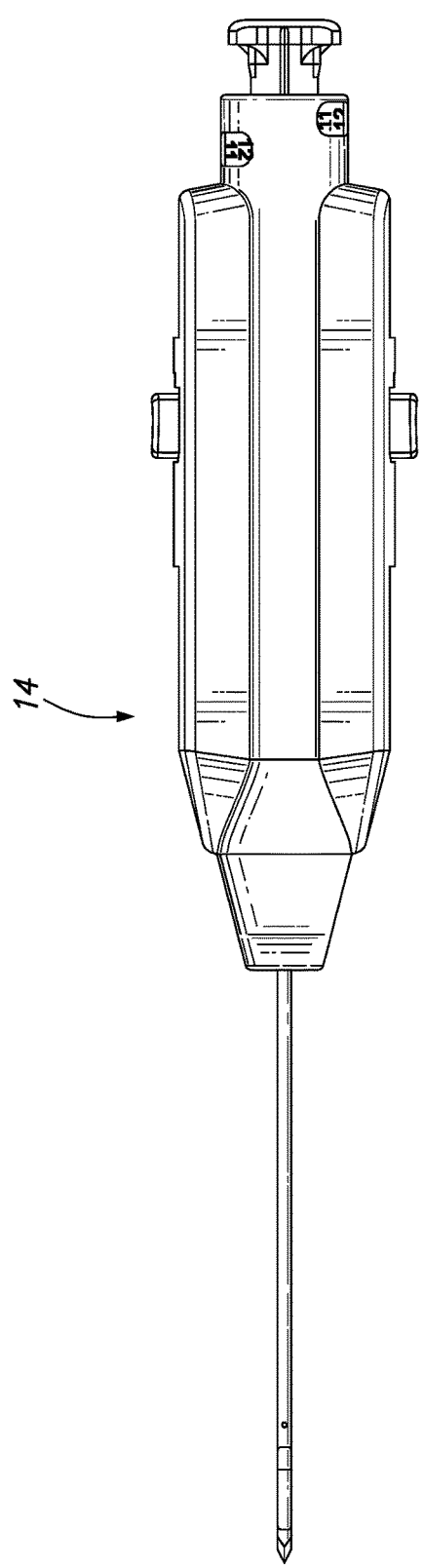
FIG. 37 is a top plan view of the needle portion of FIG. 36.

FIG. 37 is a top plan view of the needle portion of FIG. 36.

Figure 38:
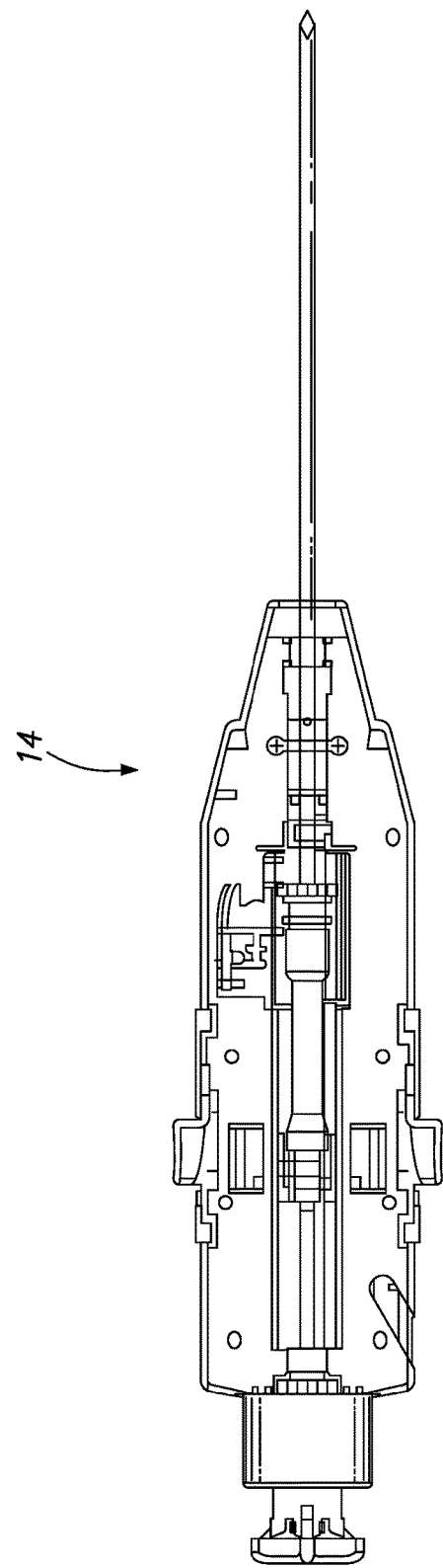
FIG. 38 is a bottom plan view of the needle portion of FIG. 36.

FIG. 38 is a bottom plan view of the needle portion of FIG. 36.

Figure 39:
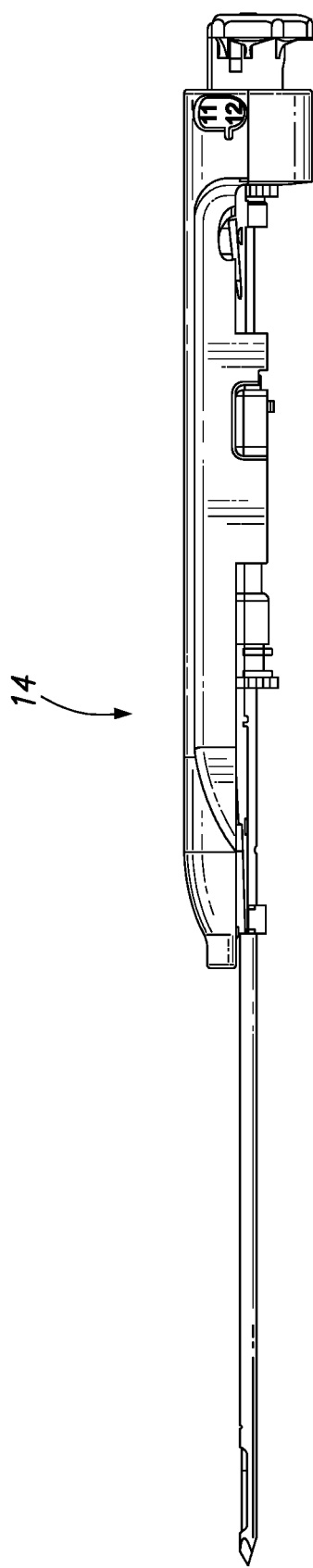
FIG. 39 is a left side elevational view of the needle portion of FIG. 36.

FIG. 39 is a left side elevational view of the needle portion of FIG. 36.

Figure 40:
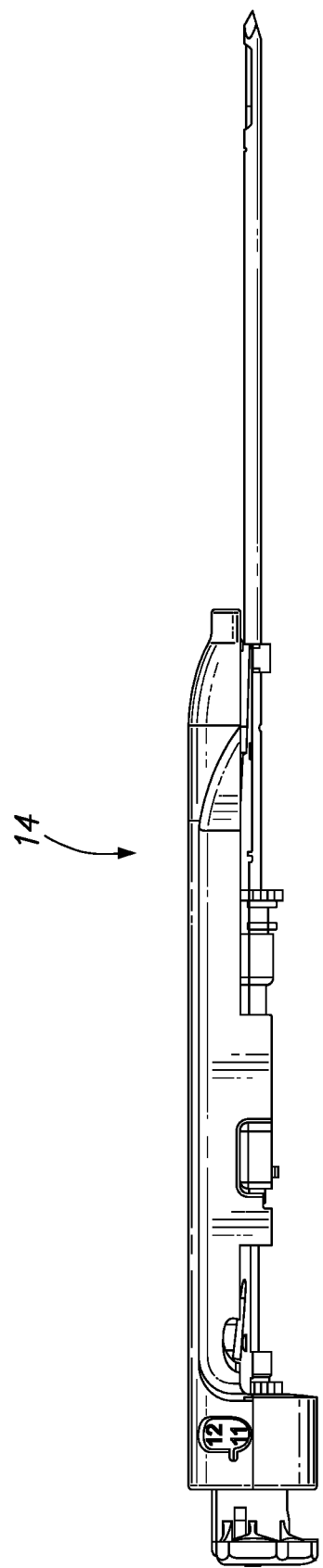
FIG. 40 is a right side elevational view of the needle portion of FIG. 36.

FIG. 40 is a right side elevational view of the needle portion of FIG. 36.

Figure 41:
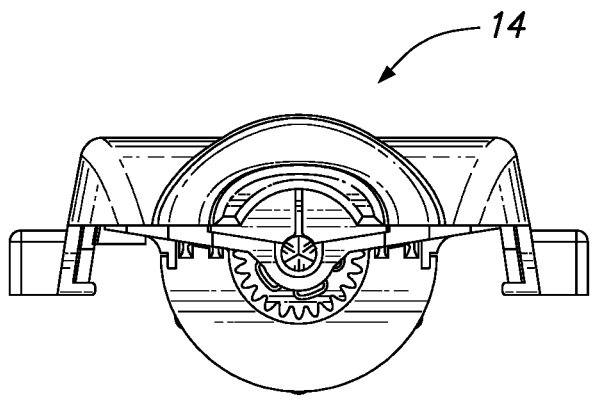
FIG. 41 is a front elevational view of the needle portion of FIG. 36.

FIG. 41 is a front elevational view of the needle portion of FIG. 36.

Figure 42:
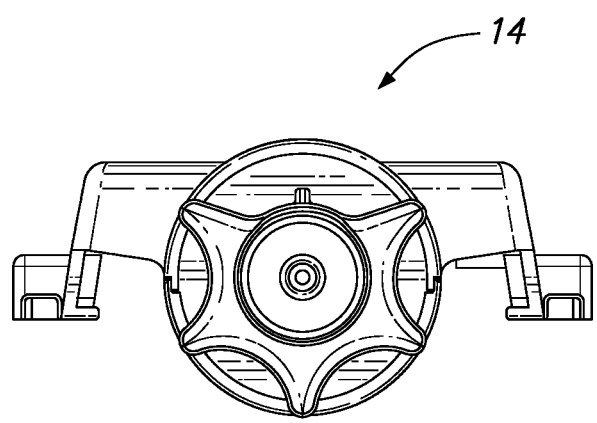
FIG. 42 is a rear elevational view of the needle portion of FIG. 36.

FIG. 42 is a rear elevational view of the needle portion of FIG. 36.

Figure 43:
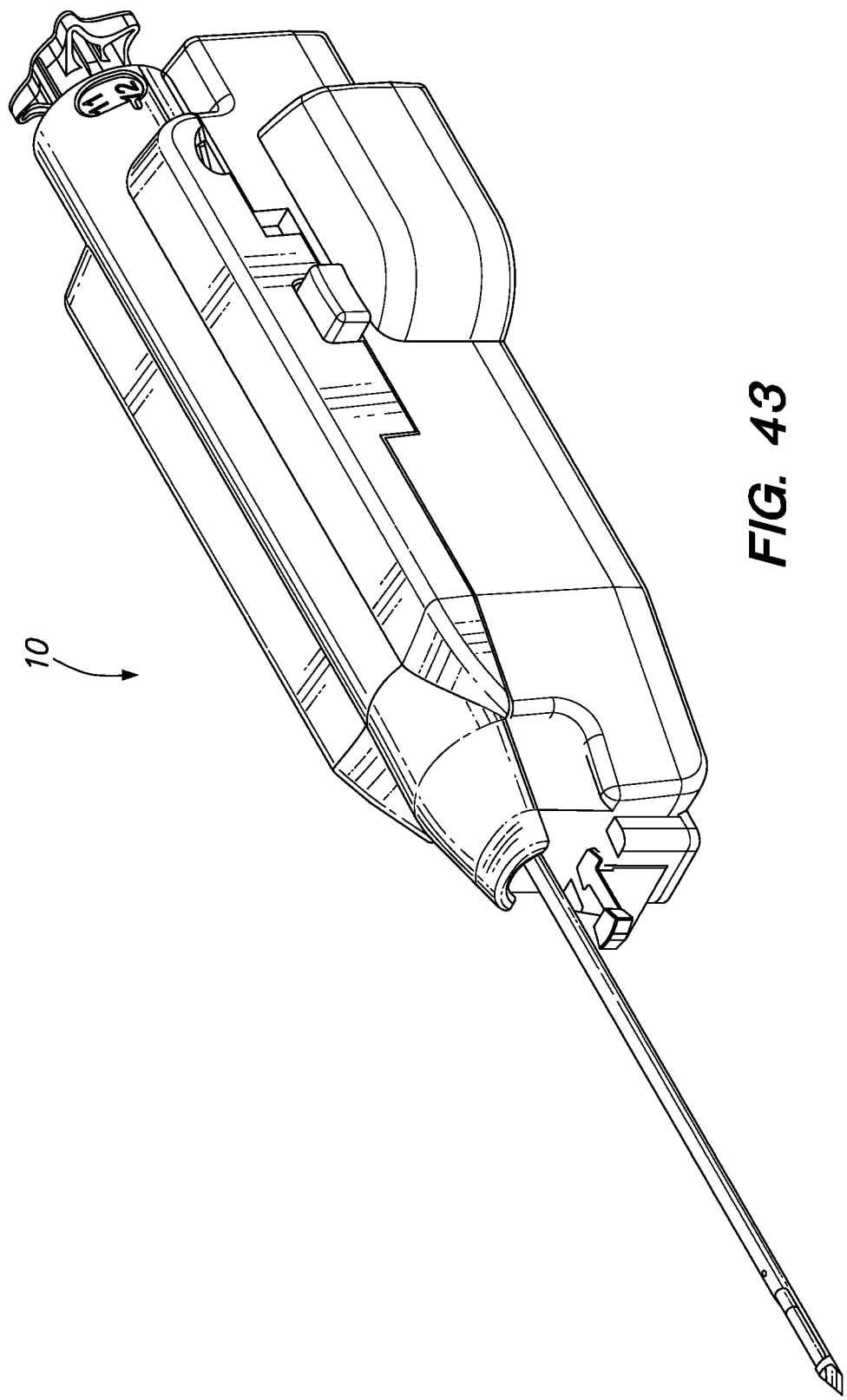
FIG. 43 is a perspective view of the needle portion of FIG. 36 attached to a body portion of a two-part biopsy device.

FIG. 43 is a perspective view of the needle portion of FIG. 36 attached to a body portion of a two-part biopsy device.

Figure 44:
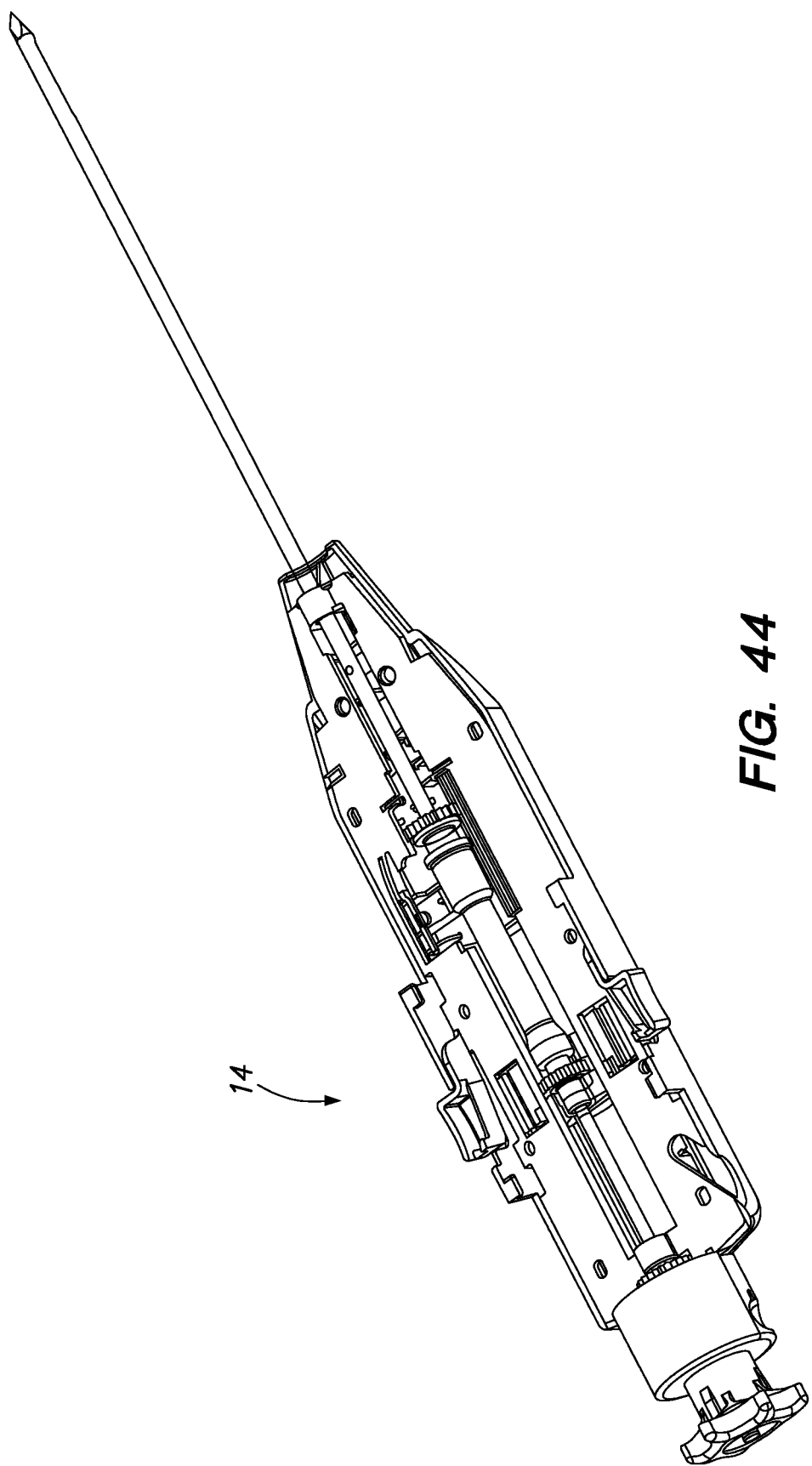
FIG. 44 is a second perspective view of the needle portion of FIG. 36.

FIG. 44 is a second perspective view of the needle portion of FIG. 36.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A method of performing a biopsy procedure on a human breast using a biopsy system, the biopsy system including a support structure, an elongate cannula coupled to and extending from the support structure, the cannula having a distal portion with a tissue receiving aperture in a side wall thereof, an axially oscillating cutter disposed in an axial lumen of the cannula, and an elongate hollow introducer, the method comprising:
characterizing the breast based on a size attribute of the breast;
releasably attaching the introducer to the support structure over the cannula in a first attachment configuration if the breast is characterized as having a first size attribute, and
releasably attaching the introducer to the support structure over the cannula in a second attachment configuration if the breast is characterized as having a second size attribute different from the first size attribute,
wherein in at least one of the first and second attachment configurations the tissue receiving aperture is partially obscured by the introducer.

2. The breast biopsy method of claim 1, further comprising
translating the cutter across the tissue receiving aperture at a first cutter stroke length if the introducer is attached to the support structure in the first attachment configuration, and
translating the cutter across the tissue receiving aperture at a second cutter stroke length less than the first stroke length if the introducer is attached to the support structure in the second attachment configuration.

3. The breast biopsy method of claim 1, wherein,
in the first attachment configuration, the distal portion of the cannula extends out an open distal end of the introducer with the tissue receiving aperture unobscured by the introducer, and
in the second attachment configuration, the distal portion of the cannula extends out the open distal end of the introducer with the tissue receiving aperture partially obscured by the introducer.

4. The breast biopsy method of claim 1, wherein the attaching the introducer in the second configuration comprises switching the introducer from the first attachment configuration to the second attachment configuration without removing the introducer from the cannula.

5. The breast biopsy method of claim 1, wherein the second size attribute corresponds to a petite size breast.

6. The breast biopsy method of claim 1, further comprising
using one or more sensors, detecting whether the introducer is attached to the support structure in the first attachment configuration or the second attachment configuration.

7. The breast biopsy method of claim 6, wherein the one or more sensors are configured to detect a locating element coupled to a proximal portion of the introducer, wherein the locating element is (i) in a first position relative to the one or more sensors when the introducer is attached to the support structure in the first attachment configuration, and (ii) in a second position relative to the one or more sensors when the introducer is attached to the support structure in the second attachment configuration.

8. The breast biopsy method of claim 7, the one or more sensors comprising laterally spaced apart first and second magnetic sensors coupled to or adjacent the support structure.

9. The breast biopsy method of claim 1, the cannula being movably coupled to the support structure between a proximal armed position and a distal fired position, the method further comprising
firing the cannula a first firing distance from the armed position to the fired position when the introducer is attached to the support structure in the first attachment configuration, and
firing the cannula a second firing distance less than the first firing distance from the armed position to the fired position when the introducer is attached to the support structure in the second attachment configuration.

10. A method of performing a biopsy procedure on a human breast using a biopsy system, the biopsy system including a support structure, an elongate cannula coupled to and extending from the support structure, the cannula having a distal portion with a tissue receiving aperture in a side wall thereof, an axially oscillating cutter disposed in an axial lumen of the cannula, and an elongate hollow introducer, the method comprising:
releasably attaching the introducer to the support structure over the cannula in one of a first attachment configuration and a second attachment configuration, wherein in at least one of the first and second attachment configurations the tissue receiving aperture is partially obscured by the introducer, and using one or more sensors, detecting whether the introducer is attached to the support structure in the first attachment configuration or the second attachment configuration.

11. The breast biopsy method of claim 10, further comprising translating the cutter across the tissue receiving aperture at a first cutter stroke length if the introducer is attached to the support structure in the first attachment configuration, and translating the cutter across the tissue receiving aperture at a second cutter stroke length less than the first stroke length if the introducer is attached to the support structure in the second attachment configuration.

12. The breast biopsy method of claim 10, wherein, in the first attachment configuration, the distal portion of the cannula extends out an open distal end of the introducer with the tissue receiving aperture unobscured by the introducer, and in the second attachment configuration, the distal portion of the cannula extends out the open distal end of the introducer with the tissue receiving aperture partially obscured by the introducer.

13. The breast biopsy method of claim 10, wherein the attaching the introducer in the second configuration comprises switching the introducer from the first attachment configuration to the second attachment configuration without removing the introducer from the cannula.

14. The breast biopsy method of claim 10, wherein the one or more sensors are configured to detect a locating element coupled to a proximal portion of the introducer, wherein the locating element is (i) in a first position relative to the one or more sensors when the introducer is attached to the support structure in the first attachment configuration, and (ii) in a second position relative to the one or more sensors when the introducer is attached to the support structure in the second attachment configuration.

15. The breast biopsy method of claim 14, the one or more sensors comprising laterally spaced apart first and second magnetic sensors coupled to or adjacent the support structure.

16. The breast biopsy method of claim 10, the cannula being movably coupled to the support structure between a proximal armed position and a distal fired position, the method further comprising firing the cannula a first firing distance from the armed position to the fired position when the introducer is attached to the support structure in the first attachment configuration, and firing the cannula a second firing distance less than the first firing distance from the armed position to the fired position when the introducer is attached to the support structure in the second attachment configuration.

* * * * *